(12) United States Patent
Clausen et al.

(10) Patent No.: US 11,147,692 B2
(45) Date of Patent: Oct. 19, 2021

(54) PROSTHETIC FEET AND FOOT COVERS

(71) Applicant: Össur Iceland ehf, Reykjavik (IS)

(72) Inventors: Arinbjörn Viggo Clausen, Reykjavik (IS); Ragnar Örn Gunnarsson, Reykjavik (IS); Bjarni Andresson, Seltjarnarnes (IS); Lárus Gunnsteinsson, Reykjavik (IS); Rowan Patrick Robinson Cain, Kopavogur (IS)

(73) Assignee: Össur Iceland ehf, Reykjavik (IS)

(*) Notice: Subject to any disclaimer, the term of this patent is extended or adjusted under 35 U.S.C. 154(b) by 0 days.

(21) Appl. No.: 15/985,484

(22) Filed: May 21, 2018

(65) Prior Publication Data

US 2018/0263793 A1    Sep. 20, 2018

Related U.S. Application Data

(62) Division of application No. 14/755,464, filed on Jun. 30, 2015, now Pat. No. 9,999,524.

(Continued)

(51) Int. Cl.
*A61F 2/66* (2006.01)
*A61F 2/50* (2006.01)

(52) U.S. Cl.
CPC ........ *A61F 2/66* (2013.01); *A61F 2002/5001* (2013.01); *A61F 2002/665* (2013.01);
(Continued)

(58) Field of Classification Search
CPC .............................................. A61F 2002/5001
See application file for complete search history.

(56) References Cited

U.S. PATENT DOCUMENTS

| 25,238 A | 8/1859 | Bly |
| 53,931 A | 4/1866 | Weston |

(Continued)

FOREIGN PATENT DOCUMENTS

| CN | 1529573 A | 9/2004 |
| CN | 1835721 A | 9/2006 |

(Continued)

OTHER PUBLICATIONS

Office Action in corresponding European Patent Application No. 15814978.1, dated May 10, 2019, in 5 pages.

(Continued)

*Primary Examiner* — Jacqueline Wozniki
(74) *Attorney, Agent, or Firm* — Knobbe, Martens, Olson & Bear, LLP

(57) ABSTRACT

Prosthetic feet and foot covers that provide a more natural appearance and improved performance are provided. A foot element for a prosthetic foot can extend from a heel end to a toe end and include a heel, arch, forefoot, and toe regions. The forefoot region can be wider than the arch and heel regions. The toe region can include a U-shaped cut out to define a big toe. Various features of the foot element can guide rollover of the foot through the big toe during use. A foot cover can be designed to receive a prosthetic foot including such a foot element. The foot cover can have a region of increased flexibility at a transition between the forefoot region and toe region. The foot cover can also have a padded area extending from the heel region across a lateral part of the arch region and forefoot region.

18 Claims, 21 Drawing Sheets

Related U.S. Application Data

(60) Provisional application No. 62/019,233, filed on Jun. 30, 2014, provisional application No. 62/153,387, filed on Apr. 27, 2015.

(52) U.S. Cl.
CPC .......... *A61F 2002/6614* (2013.01); *A61F 2002/6621* (2013.01); *A61F 2002/6628* (2013.01); *A61F 2002/6671* (2013.01)

(56) References Cited

U.S. PATENT DOCUMENTS

| | | | |
|---|---|---|---|
| 56,983 A | 8/1866 | Nicholas | |
| 57,666 A | 9/1866 | Bly | |
| 368,580 A | 8/1887 | Frees | |
| 487,697 A | 12/1892 | Ehle | |
| 511,942 A * | 1/1894 | Glainville | A43B 17/12 36/43 |
| 534,198 A | 2/1895 | Chapman | |
| 619,731 A | 2/1899 | Doerflinger et al. | |
| 808,296 A | 12/1905 | Merrick | |
| 809,876 A | 1/1906 | Wilkins | |
| 817,340 A | 4/1906 | Rosenkranz | |
| 2,003,961 A * | 6/1935 | Vittengl | A43B 13/38 36/43 |
| 2,183,076 A | 12/1939 | Kaiser | |
| 2,197,093 A | 4/1940 | Campbell | |
| 2,315,795 A | 4/1943 | Johnson et al. | |
| 2,357,893 A | 9/1944 | Harrington | |
| 2,440,075 A | 4/1948 | Campbell | |
| 2,556,525 A | 6/1951 | Drennon | |
| 2,594,945 A | 4/1952 | Lucas et al. | |
| 2,692,392 A | 10/1954 | Bennington et al. | |
| 2,731,645 A | 1/1956 | Woodall | |
| 3,098,239 A | 7/1963 | Nader | |
| 3,461,464 A | 8/1969 | Lindgren | |
| 3,551,914 A | 1/1971 | Woodall | |
| 3,784,988 A | 1/1974 | Trumpler | |
| 3,874,004 A | 4/1975 | May | |
| 3,894,437 A | 7/1975 | Nagy et al. | |
| 4,007,497 A | 2/1977 | Haupt | |
| 4,177,525 A | 12/1979 | Arbogast et al. | |
| 4,267,728 A | 5/1981 | Manley et al. | |
| 4,360,931 A | 11/1982 | Hampton | |
| 4,387,472 A | 6/1983 | Wilson | |
| 4,416,293 A | 11/1983 | Anderson et al. | |
| 4,506,395 A | 3/1985 | Haupt | |
| 4,547,913 A | 10/1985 | Phillips | |
| 4,619,661 A | 10/1986 | Axelsson | |
| 4,631,676 A | 12/1986 | Pugh | |
| 4,645,509 A * | 2/1987 | Poggi | A61F 2/66 623/55 |
| 4,652,266 A | 3/1987 | Truesdell | |
| 4,718,913 A | 1/1988 | Voisin | |
| 4,791,736 A * | 12/1988 | Phillips | A43B 5/0405 12/142 P |
| 4,813,436 A | 3/1989 | Au | |
| 4,814,661 A | 3/1989 | Ratzlaff et al. | |
| 4,822,363 A | 4/1989 | Phillips | |
| 4,858,621 A | 8/1989 | Franks | |
| 4,892,553 A | 1/1990 | Prahl | |
| 4,892,554 A | 1/1990 | Robinson | |
| 4,959,073 A | 9/1990 | Merlette | |
| 5,019,109 A | 5/1991 | Voisin | |
| 5,037,444 A | 8/1991 | Phillips | |
| 5,062,859 A | 11/1991 | Naeder | |
| 5,064,438 A | 11/1991 | Naeder | |
| 5,112,356 A | 5/1992 | Harris et al. | |
| 5,116,384 A | 5/1992 | Wilson et al. | |
| 5,116,385 A | 5/1992 | Allard et al. | |
| 5,128,880 A | 7/1992 | White | |
| 5,139,525 A | 8/1992 | Kristinsson | |
| 5,156,631 A | 10/1992 | Merlette | |
| 5,156,632 A | 10/1992 | Wellershaus | |
| 5,181,932 A | 1/1993 | Phillips | |
| 5,181,933 A | 1/1993 | Phillips | |
| 5,219,365 A | 6/1993 | Sabolich | |
| 5,237,520 A | 8/1993 | White | |
| 5,253,656 A | 10/1993 | Rincoe et al. | |
| 5,258,038 A | 11/1993 | Robinson et al. | |
| 5,258,039 A | 11/1993 | Goh et al. | |
| 5,290,319 A | 3/1994 | Phillips | |
| 5,361,133 A | 11/1994 | Brown et al. | |
| 5,376,133 A | 12/1994 | Gramnas | |
| 5,376,141 A | 12/1994 | Phillips | |
| 5,387,246 A | 2/1995 | Phillips | |
| 5,388,591 A | 2/1995 | De Luca et al. | |
| 5,408,873 A | 4/1995 | Schmidt et al. | |
| 5,425,781 A | 6/1995 | Allard et al. | |
| 5,443,522 A | 8/1995 | Sabolich | |
| 5,443,527 A | 8/1995 | Wilson | |
| 5,443,529 A | 8/1995 | Phillips | |
| 5,417,405 A | 11/1995 | Marsh | |
| 5,471,405 A | 11/1995 | Marsh | |
| 5,474,087 A | 12/1995 | Nashner | |
| 5,509,938 A | 4/1996 | Phillips | |
| 5,514,185 A | 5/1996 | Phillips | |
| 5,514,186 A | 5/1996 | Phillips | |
| 5,545,230 A | 8/1996 | Phillips | |
| 5,545,234 A | 8/1996 | Collier, Jr. | |
| 5,549,711 A | 8/1996 | Bryant | |
| 5,623,944 A | 4/1997 | Nashner | |
| 5,653,767 A | 8/1997 | Allen et al. | |
| 5,695,526 A | 12/1997 | Wilson | |
| 5,695,527 A | 12/1997 | Allen | |
| 5,701,686 A | 12/1997 | Berr et al. | |
| 5,728,177 A | 3/1998 | Phillips | |
| 5,753,931 A | 5/1998 | Borchers et al. | |
| 5,766,264 A | 6/1998 | Lundt | |
| 5,790,256 A | 8/1998 | Brown et al. | |
| 5,800,569 A | 9/1998 | Phillips | |
| 5,800,570 A | 9/1998 | Collier | |
| 5,824,112 A | 10/1998 | Phillips | |
| 5,885,229 A | 3/1999 | Yamato et al. | |
| 5,897,594 A | 4/1999 | Martin et al. | |
| 5,899,944 A | 5/1999 | Phillips | |
| 5,941,913 A | 8/1999 | Woolnough et al. | |
| 5,944,760 A | 8/1999 | Christensen | |
| 5,957,870 A | 9/1999 | Yamato et al. | |
| 5,957,981 A | 9/1999 | Gramnas | |
| 5,976,191 A | 11/1999 | Phillips | |
| 5,993,488 A | 11/1999 | Phillips | |
| 6,063,046 A | 5/2000 | Allum | |
| 6,071,313 A | 6/2000 | Phillips | |
| 6,077,301 A | 6/2000 | Pusch | |
| 6,099,572 A | 8/2000 | Mosler et al. | |
| 6,120,547 A | 9/2000 | Christensen | |
| 6,129,766 A | 10/2000 | Johnson et al. | |
| 6,165,227 A | 12/2000 | Phillips | |
| 6,187,052 B1 | 2/2001 | Molino et al. | |
| 6,197,067 B1 | 3/2001 | Shorter et al. | |
| 6,197,068 B1 | 3/2001 | Christensen | |
| 6,205,230 B1 | 3/2001 | Sundman et al. | |
| 6,206,934 B1 | 3/2001 | Phillips | |
| 6,216,545 B1 | 4/2001 | Taylor | |
| 6,231,527 B1 | 5/2001 | Sol | |
| 6,241,776 B1 | 6/2001 | Christensen | |
| 6,261,324 B1 | 7/2001 | Merlette | |
| 6,280,479 B1 | 8/2001 | Phillips | |
| 6,289,107 B1 | 9/2001 | Borchers et al. | |
| 6,290,730 B1 | 9/2001 | Pitkin et al. | |
| 6,331,893 B1 | 12/2001 | Brown et al. | |
| 6,350,286 B1 | 2/2002 | Atkinson et al. | |
| 6,387,134 B1 | 5/2002 | Parker et al. | |
| 6,398,818 B1 | 6/2002 | Merlette et al. | |
| 6,402,790 B1 | 6/2002 | Celebi | |
| 6,406,500 B1 | 6/2002 | Phillips | |
| 6,443,993 B1 | 9/2002 | Koniuk | |
| 6,443,995 B1 | 9/2002 | Townsend et al. | |
| 6,514,293 B1 | 2/2003 | Seong et al. | |
| 6,527,811 B1 | 3/2003 | Phillips | |
| 6,546,356 B1 | 4/2003 | Genest | |
| 6,596,029 B1 | 7/2003 | Gramnas | |

(56) References Cited

U.S. PATENT DOCUMENTS

| | | | |
|---|---|---|---|
| 6,602,295 B1 | 8/2003 | Doddroe et al. |
| 6,663,672 B1 | 12/2003 | Laghi |
| 6,663,673 B2 | 12/2003 | Christensen |
| 6,676,708 B1 | 1/2004 | Laghi |
| 6,699,295 B2 | 3/2004 | Lee et al. |
| 6,702,859 B1 | 3/2004 | Laghi |
| 6,702,860 B1 | 3/2004 | Laghi |
| 6,706,075 B1 | 3/2004 | Laghi |
| 6,712,860 B2 | 3/2004 | Rubie et al. |
| 6,718,656 B2 | 4/2004 | Houser et al. |
| 6,719,807 B2 | 4/2004 | Harris |
| 6,743,260 B2 | 6/2004 | Townsend et al. |
| 6,764,521 B2 | 7/2004 | Molino et al. |
| 6,764,522 B1 | 7/2004 | Cehn |
| 6,767,370 B1 | 7/2004 | Mosler et al. |
| 6,793,683 B1 | 9/2004 | Laghi |
| 6,797,009 B1 | 9/2004 | Laghi |
| 6,805,717 B2 | 10/2004 | Christensen |
| 6,807,869 B2 | 10/2004 | Farringdon et al. |
| 6,827,744 B1 | 12/2004 | Laghi |
| 6,855,170 B2 | 2/2005 | Gramnas |
| 6,869,451 B1 | 2/2005 | Laghi |
| 6,875,240 B1 | 4/2005 | Laghi |
| 6,875,241 B2 | 4/2005 | Christensen |
| 6,875,242 B2 | 4/2005 | Christensen |
| 6,899,737 B1 | 5/2005 | Phillips |
| 6,929,665 B2 | 8/2005 | Christensen |
| 6,936,074 B2 | 8/2005 | Townsend et al. |
| 6,942,704 B2 | 9/2005 | Sulprizio |
| 6,966,933 B2 | 11/2005 | Christensen |
| 6,969,408 B2 | 11/2005 | Lecomte et al. |
| 7,052,519 B1 | 5/2006 | Gramnas |
| 7,063,727 B2 | 6/2006 | Van Phillips et al. |
| 7,108,723 B2 | 9/2006 | Townsend et al. |
| 7,112,227 B2 | 9/2006 | Doddroe et al. |
| 7,169,190 B2 | 1/2007 | Phillips et al. |
| 7,172,630 B2 | 2/2007 | Christensen |
| 7,211,115 B2 | 5/2007 | Townsend et al. |
| 7,219,449 B1 | 5/2007 | Hoffberg et al. |
| 7,279,011 B2 | 10/2007 | Phillips |
| 7,318,504 B2 | 1/2008 | Viltale et al. |
| 7,337,680 B2 | 3/2008 | Kantro |
| 7,341,603 B2 | 3/2008 | Christensen |
| 7,347,877 B2 | 3/2008 | Clausen et al. |
| 7,354,456 B2 | 4/2008 | Phillips |
| 7,371,262 B2 | 5/2008 | Lecomte et al. |
| 7,374,578 B2 | 5/2008 | Townsend et al. |
| 7,410,503 B2 | 8/2008 | Townsend et al. |
| 7,419,509 B2 | 9/2008 | Christensen |
| 7,429,272 B2 | 9/2008 | Townsend et al. |
| D579,115 S | 10/2008 | Rubie et al. |
| 7,431,737 B2 | 10/2008 | Ragnarsdottir et al. |
| 7,462,201 B2 | 12/2008 | Christensen |
| 7,507,259 B2 | 3/2009 | Townsend et al. |
| 7,520,904 B2 | 4/2009 | Christensen |
| 7,531,006 B2 | 5/2009 | Clausen et al. |
| 7,572,299 B2 | 8/2009 | Christensen |
| 7,578,852 B2 | 8/2009 | Townsend et al. |
| 7,581,454 B2 | 9/2009 | Clausen et al. |
| 7,611,543 B2 | 11/2009 | Townsend et al. |
| 7,617,068 B2 | 11/2009 | Tadin et al. |
| 7,618,464 B2 | 11/2009 | Christensen |
| 7,637,659 B2 | 12/2009 | Liu et al. |
| 7,637,957 B2 | 12/2009 | Ragnarsdóttir et al. |
| 7,648,533 B2 | 1/2010 | Phillips et al. |
| 7,686,848 B2 | 3/2010 | Christensen |
| 7,708,784 B2 | 5/2010 | Townsend et al. |
| 7,727,285 B2 | 6/2010 | Christensen et al. |
| 7,771,488 B2 | 8/2010 | Asgeirsson et al. |
| 7,815,689 B2 | 10/2010 | Bedard et al. |
| 7,824,446 B2 | 11/2010 | Christensen et al. |
| 7,833,287 B2 | 11/2010 | Doddroe et al. |
| 7,846,213 B2 | 12/2010 | Lecomte et al. |
| 7,862,621 B2 | 1/2011 | Kloos et al. |
| 7,862,622 B2 | 1/2011 | Dunlap et al. |
| 7,867,285 B2 | 1/2011 | Clausen et al. |
| D632,392 S | 2/2011 | Jacobs et al. |
| 7,879,110 B2 | 2/2011 | Phillips |
| 7,891,258 B2 | 2/2011 | Clausen et al. |
| D633,618 S | 3/2011 | Johnson et al. |
| 7,926,363 B2 | 4/2011 | Miller et al. |
| 7,951,100 B2 | 5/2011 | Pusch |
| 7,955,399 B2 | 6/2011 | Townsend et al. |
| 7,998,221 B2 | 8/2011 | Lecomte et al. |
| 8,007,544 B2 | 8/2011 | Jonsson et al. |
| 8,025,699 B2 | 9/2011 | Lecomte et al. |
| D647,617 S | 10/2011 | Mile |
| 8,034,121 B2 | 10/2011 | Christensen |
| 8,048,172 B2 | 11/2011 | Jonsson et al. |
| 8,070,829 B2 | 12/2011 | Townsend et al. |
| 8,075,501 B2 | 12/2011 | Miller et al. |
| D653,759 S | 2/2012 | Smith et al. |
| D655,009 S | 2/2012 | L'heureux |
| 8,109,014 B2 | 2/2012 | Miller et al. |
| 8,117,922 B2 | 2/2012 | Xia et al. |
| 8,128,709 B2 | 3/2012 | Thorhallsdottir et al. |
| 8,261,611 B2 | 9/2012 | Kim et al. |
| 8,290,739 B2 | 10/2012 | Tadin et al. |
| 8,409,014 B2 | 4/2013 | Gagner et al. |
| 8,486,156 B2 | 7/2013 | Jonsson |
| 8,500,825 B2 | 8/2013 | Christensen et al. |
| D689,505 S | 9/2013 | Convay et al. |
| 8,544,347 B1 | 10/2013 | Berme |
| 8,771,372 B1 | 7/2014 | Rubie et al. |
| 9,017,421 B2 | 4/2015 | Lecomte et al. |
| D731,062 S | 6/2015 | Meyer et al. |
| 9,132,022 B2 | 9/2015 | Lecomte et al. |
| 9,668,887 B2 | 6/2017 | Lecomte et al. |
| D795,433 S | 8/2017 | Clausen et al. |
| D797,292 S | 9/2017 | Clausen et al. |
| 9,999,524 B2 | 6/2018 | Clausen et al. |
| 2002/0013628 A1 | 1/2002 | Harris |
| 2002/0040249 A1 | 4/2002 | Phillips |
| 2002/0077706 A1 | 6/2002 | Phillips |
| 2002/0082713 A1 | 6/2002 | Townsend et al. |
| 2002/0087216 A1 | 7/2002 | Atkinson et al. |
| 2002/0116072 A1 | 8/2002 | Rubie et al. |
| 2002/0128727 A1 | 9/2002 | Merlette et al. |
| 2002/0138923 A1 | 10/2002 | Shaffeeullah |
| 2002/0143408 A1 | 10/2002 | Townsend et al. |
| 2002/0183860 A1 | 12/2002 | Wilkinson et al. |
| 2003/0009911 A1* | 1/2003 | Brown .................. A43B 7/141 36/29 |
| 2003/0045944 A1 | 5/2003 | Mosler et al. |
| 2003/0093158 A1* | 5/2003 | Phillips .................. A61F 2/66 623/52 |
| 2003/0120353 A1 | 6/2003 | Christensen |
| 2003/0144745 A1 | 7/2003 | Phillips |
| 2003/0191540 A1 | 10/2003 | Townsend et al. |
| 2004/0064195 A1 | 4/2004 | Herr |
| 2004/0068327 A1 | 4/2004 | Christensen |
| 2004/0102726 A1* | 5/2004 | Sullivan .................. A61F 5/14 602/23 |
| 2004/0112138 A1 | 6/2004 | Knirck et al. |
| 2004/0122529 A1 | 6/2004 | Townsend et al. |
| 2004/0181289 A1 | 9/2004 | Bedard et al. |
| 2004/0225376 A1 | 11/2004 | Townsend et al. |
| 2005/0033451 A1 | 2/2005 | Aigner et al. |
| 2005/0038524 A1 | 2/2005 | Jonsson et al. |
| 2005/0038525 A1* | 2/2005 | Doddroe .................. A61F 2/66 623/55 |
| 2005/0060045 A1 | 3/2005 | Smith et al. |
| 2005/0071018 A1 | 3/2005 | Phillips |
| 2005/0097970 A1 | 5/2005 | Nurse |
| 2005/0107889 A1 | 5/2005 | Bedard et al. |
| 2005/0109563 A1 | 5/2005 | Vitale et al. |
| 2005/0119763 A1 | 6/2005 | Christensen |
| 2005/0137717 A1 | 6/2005 | Gramnäs et al. |
| 2005/0171618 A1 | 8/2005 | Christensen |
| 2005/0187640 A1 | 8/2005 | Christensen |
| 2005/0203640 A1 | 9/2005 | Christensen |
| 2005/0216097 A1 | 9/2005 | Rifkin |
| 2005/0234563 A1 | 10/2005 | Phillips |

(56) References Cited

U.S. PATENT DOCUMENTS

| | | | |
|---|---|---|---|
| 2005/0267603 A1* | 12/2005 | Lecomte | A61F 2/66 623/52 |
| 2006/0004467 A1 | 1/2006 | Lecomte et al. | |
| 2006/0015192 A1* | 1/2006 | Clausen | A61F 2/66 623/55 |
| 2006/0030950 A1 | 2/2006 | Townsend et al. | |
| 2006/0041321 A1 | 2/2006 | Christensen | |
| 2006/0069450 A1 | 3/2006 | McCarvill et al. | |
| 2006/0167563 A1 | 7/2006 | Johnson et al. | |
| 2006/0173555 A1 | 8/2006 | Harn et al. | |
| 2006/0212131 A1 | 9/2006 | Curtis | |
| 2006/0247794 A1 | 11/2006 | Doddroe et al. | |
| 2007/0027557 A1 | 2/2007 | Jonsson et al. | |
| 2007/0039205 A1 | 2/2007 | Peveto et al. | |
| 2007/0043582 A1 | 2/2007 | Peveto et al. | |
| 2007/0100465 A1 | 5/2007 | Egan | |
| 2007/0106395 A9* | 5/2007 | Clausen | A61F 2/66 623/52 |
| 2007/0213840 A1 | 9/2007 | Townsend et al. | |
| 2007/0219643 A1 | 9/2007 | Townsend | |
| 2007/0250178 A1 | 10/2007 | Wilson | |
| 2007/0255427 A1 | 11/2007 | Kloos et al. | |
| 2008/0033578 A1 | 2/2008 | Christensen | |
| 2008/0033579 A1 | 2/2008 | Phillips et al. | |
| 2008/0046096 A1 | 2/2008 | Bedard et al. | |
| 2008/0167730 A1 | 7/2008 | Pusch | |
| 2008/0183301 A1 | 7/2008 | Christensen | |
| 2008/0188950 A1 | 8/2008 | Fleury et al. | |
| 2008/0188951 A1 | 8/2008 | Christensen et al. | |
| 2008/0228288 A1 | 9/2008 | Nelson et al. | |
| 2008/0281436 A1 | 11/2008 | Townsend et al. | |
| 2008/0312752 A1 | 12/2008 | Miller | |
| 2009/0012630 A1 | 1/2009 | Mosler et al. | |
| 2009/0043403 A1 | 2/2009 | Asgeirsson et al. | |
| 2009/0049712 A1* | 2/2009 | Steszyn | A43B 7/1425 36/91 |
| 2009/0076626 A1 | 3/2009 | Ochoa | |
| 2009/0105845 A1 | 4/2009 | Curtis | |
| 2009/0157197 A1 | 6/2009 | Bonacini | |
| 2009/0204229 A1 | 8/2009 | Mosley et al. | |
| 2009/0204231 A1 | 8/2009 | Bonacini | |
| 2009/0222105 A1 | 9/2009 | Clausen | |
| 2009/0234463 A1 | 9/2009 | Wilson | |
| 2009/0293641 A1 | 12/2009 | Clausen et al. | |
| 2010/0004757 A1 | 1/2010 | Clausen et al. | |
| 2010/0023135 A1 | 1/2010 | Rubie et al. | |
| 2010/0042228 A1 | 2/2010 | Doddroe et al. | |
| 2010/0312360 A1 | 12/2010 | Caspers | |
| 2010/0324699 A1 | 12/2010 | Herr et al. | |
| 2011/0093089 A1 | 4/2011 | Martin | |
| 2011/0146396 A1 | 6/2011 | Kim et al. | |
| 2011/0213471 A1* | 9/2011 | Jonsson | A61F 2/66 623/53 |
| 2011/0230976 A1 | 9/2011 | Zarling et al. | |
| 2011/0251520 A1 | 10/2011 | Shieh et al. | |
| 2011/0288448 A1 | 11/2011 | Sanders et al. | |
| 2012/0023776 A1 | 2/2012 | Skaja et al. | |
| 2012/0035509 A1 | 2/2012 | Wilson et al. | |
| 2012/0151794 A1 | 6/2012 | Hansen et al. | |
| 2012/0166091 A1 | 6/2012 | Kim et al. | |
| 2012/0266648 A1 | 10/2012 | Berme et al. | |
| 2012/0271434 A1 | 10/2012 | Friesen et al. | |
| 2013/0018282 A1 | 1/2013 | Mainini et al. | |
| 2013/0060349 A1 | 3/2013 | Thorsteinsson et al. | |
| 2015/0018741 A1* | 1/2015 | Lieberson | A43B 7/144 602/28 |
| 2016/0067059 A1 | 3/2016 | Lecomte et al. | |
| 2017/0006961 A1* | 1/2017 | Pedersen | A43B 7/142 |

FOREIGN PATENT DOCUMENTS

| | | |
|---|---|---|
| CN | 1988861 A | 6/2007 |
| DE | 298 20 904 | 4/1999 |
| WO | WO 2000-27317 | 5/2000 |
| WO | WO 02/051342 | 7/2002 |
| WO | WO 2004-032809 | 4/2004 |
| WO | WO 2005/048887 | 6/2005 |
| WO | WO 2011/106564 | 9/2011 |
| WO | WO 2016-004090 | 1/2016 |

OTHER PUBLICATIONS

Office Action in corresponding Chinese Patent Application No. 201580042739.1, dated Mar. 1, 2019, in 20 pages.

Apr. 25, 2011 International Search Report and Written Opinion for International Application No. PCT/US11/26124 filed Feb. 24, 2011.

College Park Truper product, http://www.college-park.com/prostheties/truper, believed to have been available more than one year before Jun. 30, 2014.

College Park Velocity™ brochure, http://www.college-park.com/images/pdf/cpi-product-velocity.pdf, believed to have been released in 2011.

Brochure for College Park Venture Prosthetic Foot; http://www.college/park.com/assets/pdf/VentureInfoSheets.pdf, © 2003, and www.college/park.com/CPStore/ProductInfoVenture.asp; available before Aug. 15, 2003.

Feb. 7, 2013 International Search Report and Written Opinion for International Application No. PCT/US2012/066888 filed on Nov. 28, 2012.

Freedom Innovations Runway product, http://www.freedom-innovations.com/runway-2/, believed to have been available more than one year before Jun. 30, 2014.

International Search Report dated Apr. 28, 2006 for PCT/US2005/017884 filed May 20, 2006.

Ohio Willow Wood Trailblazer™ product, http://www.willowwoodco.com/products-and-services/feet/high-activity/trailblazer, believed to have been released in 2006.

Ossur Axia product, Ossur Prosthetics Catalog, pp. 153-156, 2005.

Ossur Elation product; http://www.ossur.com/template1.asp?pageid=263 and product catelog pp. 193/196; available before Aug. 15, 2003.

Otto Bock Aqua-foot product; http://professionals.ottobockus.com/cps/rde/xchg/ob_us_en/hs.xsl/41337.html, believed to have been available more than one year before Jun. 30, 2014.

Otto Bock Triton foot, http://professionals.ottobockus.com/cps/rde/xchg/ob_us_en/hs.xsl/38130.html?id=38132#t38132, believed to have been available more than one year before Jun. 30, 2014.

Otto Bock Triton products, http://www.ottobock.com/cps/rde/xchg/ob_com_en/hs.xsl/38134.html, believed to have been released Jun. 2011.

Otto Bock, Axtion product; http://www.ottobockus.com/products/lower_limb_prosthetics/axtion.asp; believed to have been released May 2004.

Trulife Seattle Kinetic product, http://trulife.com/all-products/prosthetics/feet/seattle-kinetic, believed to have been available more than one year before Jun. 30, 2014.

Dec. 8, 2015 International Search Report and Written Opinion for International Application No. PCT/US2015/38641 Filed on Jun. 30, 2015.

Ossur, Prosthetics Product Catalog, Vari-Flex®, 2005, in 9 pages.

Ossur, Prosthetics Product Catalog, K2 Sensation®, 2005, in 3 pages.

Extended Search Report in corresponding European Application No. 15814978, dated Feb. 5, 2018, in 7 pages.

Office Action in corresponding Chinese Patent Application No. 201580042739.1, dated Dec. 1, 2017, in 18 pages.

Office Action in corresponding Chinese Patent Application No. 201580042739.1, dated Jul. 23, 2018, in 12 pages.

* cited by examiner

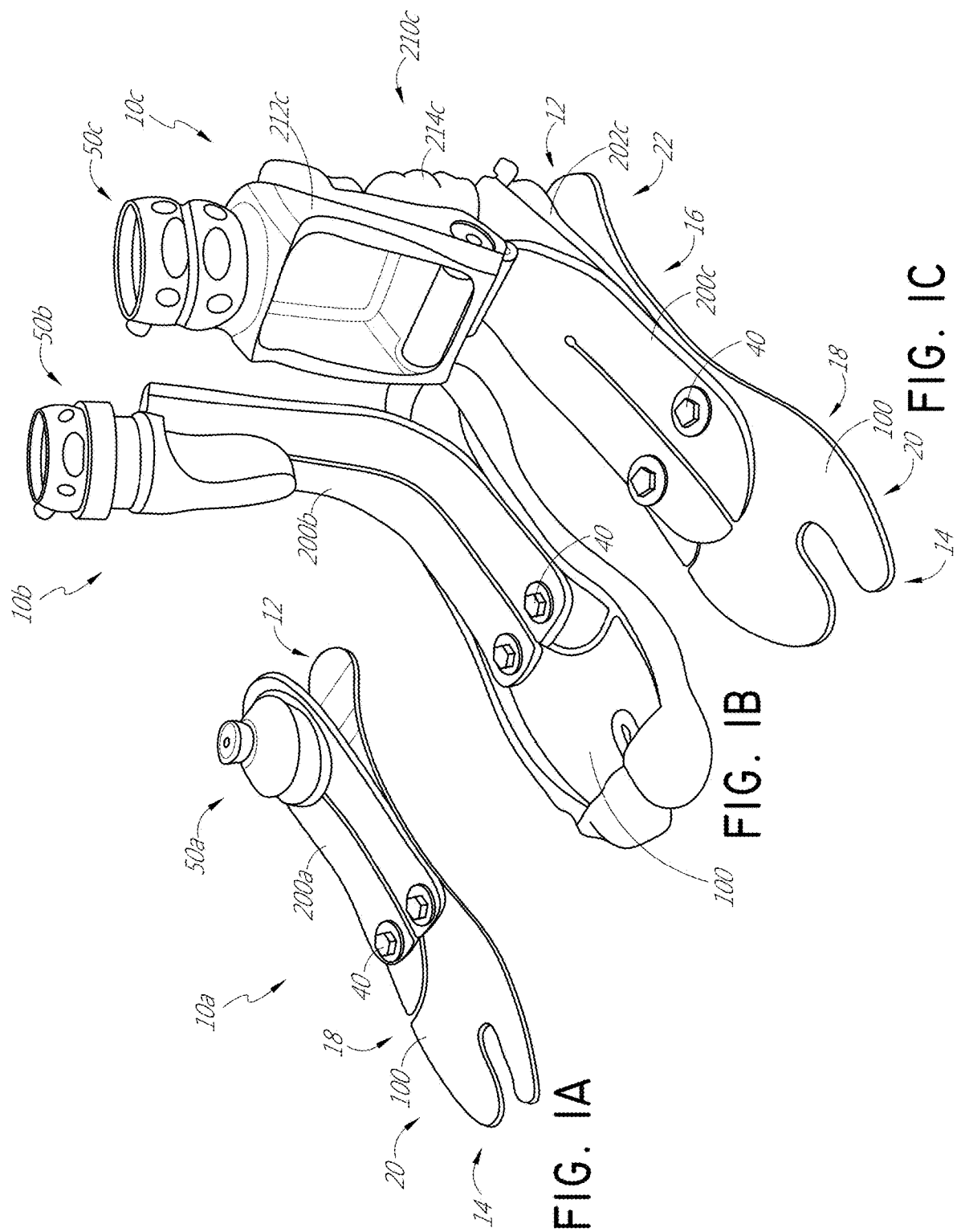

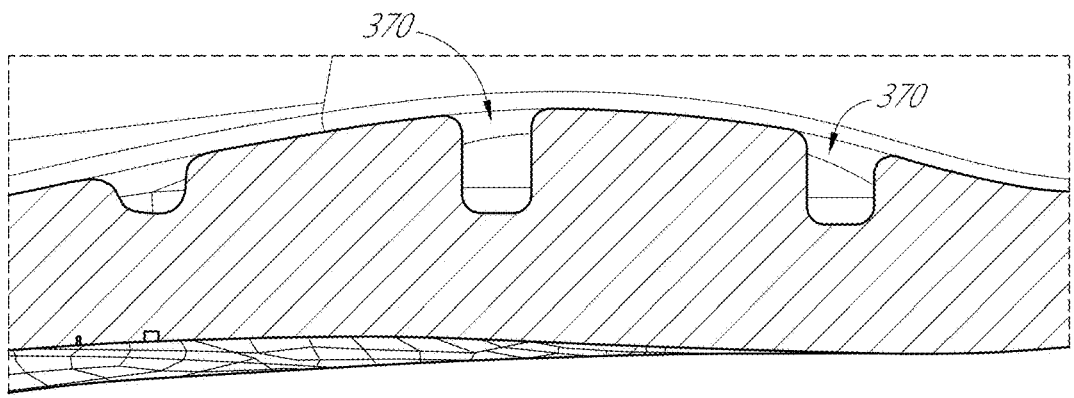
FIG. IIA
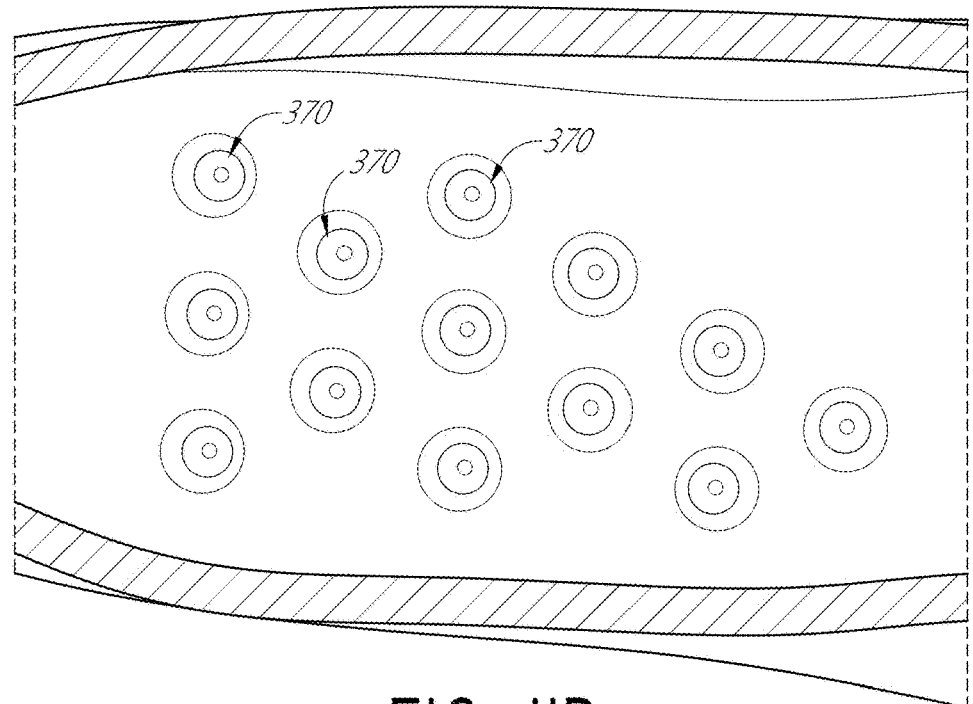
FIG. IIB

PROSTHETIC FEET AND FOOT COVERS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a divisional of U.S. patent application Ser. No. 14/755,464, filed Jun. 30, 2015, which claims the priority benefit of U.S. Provisional Application No. 62/019,233, filed Jun. 30, 2014, and 62/153,387, filed Apr. 27, 2015, the entireties of which are hereby incorporated by reference herein and should be considered part of this specification.

BACKGROUND

Field

The present disclosure relates generally to prosthetic feet and foot covers for prosthetic feet. In some embodiments, the present disclosure relates more specifically to prosthetic feet and foot covers having characteristics that provide improved rollover and/or performance.

Description of the Related Art

Various types of prosthetic foot and cosmesis devices are available as substitutes for human feet. Many prosthetic devices available today incorporate various features to try to better approximate the functioning of natural feet. For example, some prosthetic foot designs seek to provide improved foot rollover during use.

SUMMARY

In some embodiments, a prosthetic foot includes an elongate foot element extending from a heel end to a toe end and having an arch portion therebetween. In some embodiments, a ratio of a width of at least a portion of a forefoot portion of the foot element relative to a length of the foot element is approximately 30%. The foot element can further include a generally U-shaped cut-out portion at the toe end. The cut-out portion is positioned toward a medial side of a longitudinal axis of the foot element and divides the toe end into a medial toe and a lateral toe portion. The medial toe is longer and extends further distally than the lateral toe portion. The foot element can also include a lengthwise split. A first portion of the split runs substantially straight in an anterior/posterior direction, and a second portion is curved. In some embodiments, the second portion curves in a medial direction and extends to a base of the cut-out portion. In some embodiments, the second portion of the split curves in a medial direction and extends to a medial edge of the foot element in the forefoot portion. Alternatively, the second portion can curve in a lateral direction and extend to a lateral edge of the foot element in the forefoot portion.

In some embodiments, the split begins in a circular opening. A ratio of the diameter of the opening to the width of the split can be between 2:1 and 6:1. The foot element can also include an upper foot element coupled to the foot element via fasteners inserted through one or more attachment holes in the foot element. The second portion of the split can begin distal to the attachment holes. In some embodiments, the second portion of the split begins at a transition between the arch region and forefoot portion. A length of the split can be about 70% to about 90% of a total length of the foot element.

In some embodiments, a cosmesis cover for a prosthetic foot includes a body having an outer surface and surrounding an inner cavity. The outer surface has the shape and contours of a natural human foot, and the inner cavity is configured to removably receive a prosthetic foot therein. The cosmesis has a heel region, arch region, forefoot region, and toe region. The forefoot region is wider than the heel region and the arch region. The body includes a region of increased flexibility at a transition between the forefoot region and the toe region.

In some embodiments, the region of increased flexibility is thinner than a remainder of the body. A width of the forefoot region relative to a length of the cosmesis cover can be about 30%. In some embodiments, the cosmesis cover further includes a padded area extending from the heel region and across a lateral region of the arch region and the forefoot region.

In some embodiments, a prosthetic foot includes an elongate foot element and a cosmesis cover. The foot element extends from a heel end to a toe end, and a width of a forefoot portion of the foot element is greater than a width of an arch region and a heel region. The foot element can also include a generally U-shaped cut-out portion at the toe end positioned toward a medial side of a longitudinal axis of the foot element. The cut-out portion divides the toe end into a medial toe and a lateral toe portion, and the medial toe is longer and extends further distally than the lateral toe portion. The cosmesis cover includes a body having an outer surface and surrounding an inner cavity. The outer surface has the shape and contours of a natural human foot, and the inner cavity is configured to removably receive the foot element therein. The cosmesis has a heel region, arch region, forefoot region, and toe region. The forefoot region is wider than the heel region and the arch region. The cosmesis has an inner sole portion and a sidewall extending upward from the inner sole portion. A size and shape of the inner sole portion and portion of the sidewall adjacent the inner sole portion substantially corresponds to a size and shape of the foot element.

In some embodiments, the toe region of the cosmesis further includes a mating structure configured to engage the cut-out portion of the foot element. In some embodiments, the sidewall extends upward to approximately the level of an ankle of a natural human foot. Alternatively, the sidewall can extend upward to a level above or below the level of an ankle of a natural human foot. In some embodiments, a width of the forefoot portion relative to a length of the foot element is about 30%. A width of the forefoot region relative to a length of the cosmesis cover can also be about 30%.

In some embodiments, a prosthetic foot includes an elongate foot element and a forefoot piece. The elongate foot element extends from a heel end to a toe end and has an arch portion, a forefoot region, and a toe portion. The forefoot piece is coupled to a bottom surface of at least a portion of the forefoot region and the toe portion, and a bottom surface of the forefoot piece is downwardly facing convex and comprises a curvature different than a curvature of a bottom surface of a portion of the foot element proximal to the forefoot piece.

In some embodiments a ratio of a width of at least a portion of the forefoot region relative to a length of the foot element is approximately 30%. In some embodiments, the foot element includes a generally U-shaped cut-out portion at the toe end that is positioned toward a medial side of a longitudinal axis of the foot element such that the cut-out portion divides the toe end into a medial toe and a lateral toe portion, and the forefoot piece includes a generally U-shaped cut-out portion configured to correspond in size and shape to the cut-out portion of the foot element. In some embodiments, the foot element further includes a lengthwise split, wherein a first portion of the split runs substantially straight in an anterior/posterior direction and a second portion of the split curves in a medial direction and continues to a base of the cut-out portion.

In some embodiments, a prosthetic foot includes an elongate foot element and a cosmesis cover. The elongate foot element extends from a heel end to a toe end and includes a generally U-shaped cut-out portion at the toe end that is positioned toward a medial side of a longitudinal axis of the foot element such that the cut-out portion divides the toe end into a medial toe and a lateral toe portion. The medial toe is angled toward the U-shaped cut-out portion. The cosmesis cover includes a body having an outer surface and an inner surface and surrounding an inner cavity, the outer surface has the shape and contours of a natural human foot, and the inner cavity is configured to removably receive the foot element therein. The cosmesis cover includes a toe region having a slot that divides the toe region into a medial toe and a lateral toe portion and is configured to be disposed in the U-shaped cut-out portion when the foot element is disposed within the cosmesis cover. When the foot element is disposed in the cosmesis cover, the angled medial toe of the foot element forces the medial toe of the cosmesis cover toward the lateral toe portion to at least partially close the slot. In some embodiments, a portion of the medial toe of the cosmesis cover adjacent the slot has a thickness greater than a thickness of surrounding areas of the body of the cosmesis cover.

In some embodiments, a cosmesis cover for a prosthetic foot includes a body having an outer surface and surrounding an inner cavity, the body has a top opening extending into the inner cavity, the top opening is concave and a rim of the body surrounding the top opening includes cavities configured to receive pins of an attachment plate, the outer surface has the shape and contours of a natural human foot, and the inner cavity is configured to removably receive a prosthetic foot therein. In some embodiments, the cosmesis cover further includes a generally straight attachment plate including downwardly extending pins configured to be received in the cavities in the rim of the cosmesis cover body.

In some embodiments, a cosmesis cover for a prosthetic foot includes a body having an outer surface and surrounding an inner cavity, the outer surface has the shape and contours of a natural human foot, the inner cavity is configured to removably receive the prosthetic foot therein, the cosmesis body has a sole portion and a sidewall extending upward from the sole portion, and an inner surface of the sole portion includes a plurality of dimples configured to reduce distortion of the cosmesis cover during cooling during manufacture.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIGS. 1A-1F illustrate example embodiments of prosthetic feet;

FIGS. 11A-11B illustrate cross-sectional views of a foot element including dimples in a sole portion;

DETAILED DESCRIPTION

Figure 1E:
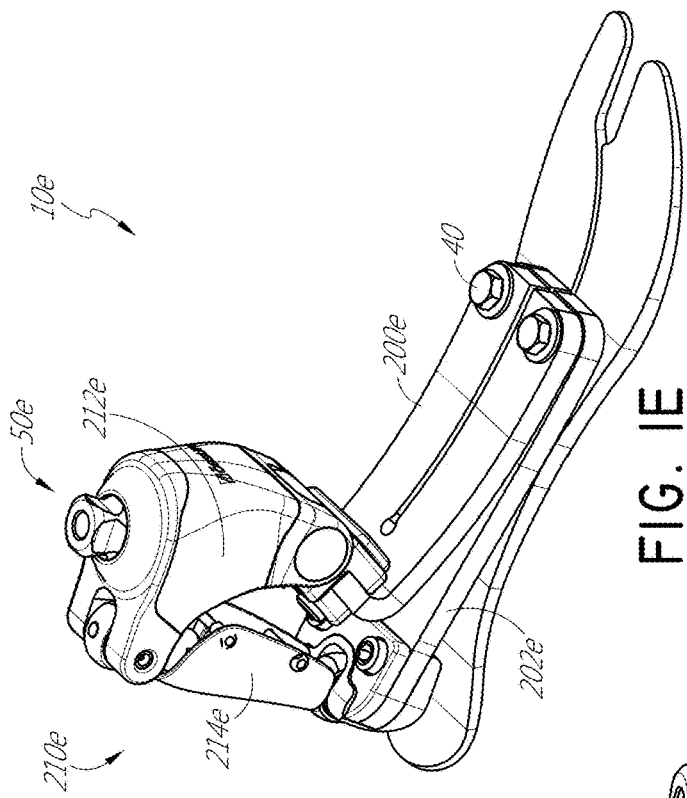

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

FIGS. 1A-1F illustrate various example embodiments of prosthetic feet 10*a*, 10*b*, 10*c*, 10*d*, 10*e*, 10*f* that can exhibit improved rollover and/or other performance characteristics in use. In some embodiments, prosthetic feet according to the present disclosure, such as the feet shown in FIG. 1, include features that allow the feet to resemble natural human feet more closely in appearance and/or rollover performance than previously available prosthetic feet. In some embodiments, a prosthetic foot 10*a*, 10*b*, 10*c*, 10*d*, 10*e*, 10*f* includes a foot element 100 (e.g., a lower foot member) as shown in the example embodiments of FIG. 1. In the illustrated embodiments, the foot element 100 is substantially plate-like and has a generally rectangular or rectangular cross-section along at least a portion of its length.

In some embodiments, the foot element 100 is constructed of a resilient material capable of flexing in multiple directions. The foot element 100 can include multiple layers or laminae. Examples of possible materials for the foot element 100 include carbon, any polymer material, and any composite of polymer and fiber. The polymer can be thermoset or thermoplastic. In a composite, the fiber reinforcement can be any type of fiber, such as carbon, glass, or aramid. The fibers can be long and unidirectional, or they can be chopped and randomly oriented.

The foot element 100 extends from a heel end 12 to a toe end 14. The foot element 100 includes an arch region 16 between the heel end 12 and the toe end 14, for example, at approximately the location of an arch of a natural human foot. The foot element 100 further includes a forefoot region 18 distal to the arch region 16 or between the arch region 16 and the toe end 14.

FIGS. 2A-4C illustrate example embodiments of foot elements 100a, 100b, 100c. In some embodiments, the forefoot region 18 of the foot element 100a, 100b, 100c is wider than a remainder of the foot element 100a, 100b, 100c, for example, wider than the arch region 16 and/or a heel region 22. The forefoot region 18 can be wider than a forefoot region of previously available prosthetic feet. For example, in some previously available prosthetic feet, the ratio of the width of the forefoot region to the length of the foot element is about 25-26%. In some prosthetic feet according to the present disclosure, the ratio of the width of the forefoot region 18 to the length of the foot element is about 30%.

In some embodiments, a toe portion 20 of the foot element 100a, 100b, 100c includes a generally U-shaped cut-out portion, slot or gap 24 extending inwardly from the toe end 14. In some embodiments, the cut-out 24 is positioned toward a medial side of a longitudinal axis of the foot element 100a, 100b, 100c, but is spaced from a medial edge 31 of the foot element 100a, 100b, 100c (e.g., the cut-out portion or gap 24 is defined between the longitudinal axis and medial edge 31 of the foot element 100a, 100b, 100c). The cut-out 24 gives the foot element 100a, 100b, 100c a "sandal toe" appearance and/or function and defines a structural "big toe" 26. The cut out portion 24 can receive a strap of a sandal. Because the forefoot region 18 is wider than a remainder of the foot element and wider than previously available prosthetic feet, the cut-out 24 and big toe 26 can be offset from the longitudinal axis of the foot element to a greater extent. In the illustrated embodiment, the big toe 26 is longer (e.g., extends further distally) than the remaining "toes" or the remainder of the toe portion 20.

In a healthy human foot, the center of mass travels approximately through the big toe and second toe as the foot rolls over from heel strike to toe off. The big toe 26 of the foot element 100a, 100b, 100c is designed to be weight-bearing and absorb load during rollover of the foot during use. In some embodiments, the big toe 26 is thicker than the remainder of the foot element 100a, 100b, 100c and/or than previously available prosthetic feet to provide additional strength. In some embodiments, the big toe 26 is formed of a particular material layup that provides the big toe 26 with strength. As described above, the big toe 26 is also longer than the remainder of the toe portion 20 and is offset from the longitudinal axis of the foot element to a greater extent than previously available prosthetic feet. These features advantageously provide the foot element 100a, 100b, 100c with a full length toe lever and allow the foot element 100a, 100b, 100c to more closely approximate or mimic a natural human foot during rollover. The outwardly bulging or curving lateral edge 33 of the forefoot region 18 of the foot element 100a, 100b, 100c can help guide the travel of the foot's center of mass toward the medial side during rollover so that the center of mass travels through the big toe 26. The cut-out portion 24 can provide the toe portion 20 of the foot element 100a, 100b, 100c with a lesser stiffness on the medial side, which also helps guide the center of mass toward the medial side during rollover. Any or all of these features can advantageously improve the rollover characteristics of the foot and provide the foot with a rollover more similar to that of a healthy, natural human foot.

Figure 5:
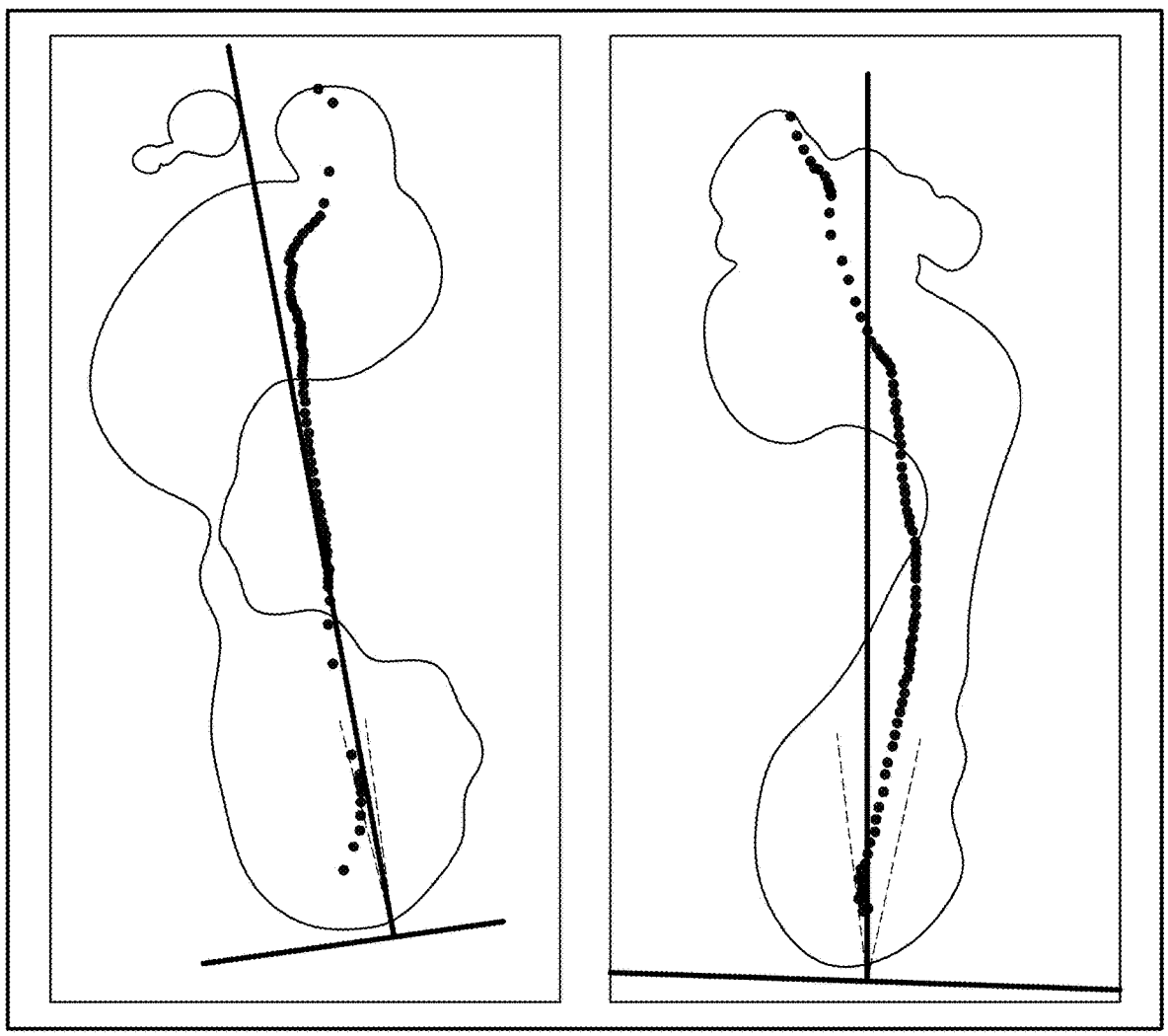
FIG. 5 illustrates a scan of the center of pressure of a sound foot and a prosthetic foot during rollover.

FIG. 5 illustrates a scan of the pressure applied by the foot to a walking surface as the foot rolls over from heel strike to toe off. The image on the left maps the pressure applied by a sound or healthy human foot, and the image on the right maps the pressure applied by a prosthetic foot including a foot element 100a and a foot cover as described herein. The dots in each image follow the path of the center of pressure as it travels through rollover. The foot element 100a, 100b, 100c advantageously provides an improved distribution of pressure in the forefoot and big toe region that more closely approximates or mimics that of a natural human foot. Additional details on prosthetic feet having features that improve rollover can be found in U.S. Pat. No. 7,846,213, entitled "Foot Prosthesis with Resilient Multi-Axial Ankle," the entirety of which is hereby incorporated by reference and should be considered a part of this specification.

In some embodiments, the foot element 100a, 100b, 100c includes a split 30a, 30b, 30c that at least partially extends substantially along the longitudinal axis of the foot. The split 30a, 30b, 30c provides a narrow gap between a medial portion 32a, 32b, 32c and a lateral portion 34a, 34b, 34c of the foot element 100a, 100b, 100c. In the illustrated embodiments, the split 30a, 30b, 30c does not extend to the heel end 12 of the foot element 100a, 100b, 100c. In some embodiments, the split 30a, 30b, 30c begins in a rounded fillet, hole, or opening 36 that helps prevent the formation of stress concentrations in that region. Although in the illustrated embodiments, the opening 36 is circular, the opening 36 can be any shape. In some such embodiments, the opening 36 is sized such that a ratio of the diameter of the opening 36 to the width of the split 30a, 30b, 30c is between 2:1 to 6:1.

Figure 2A:
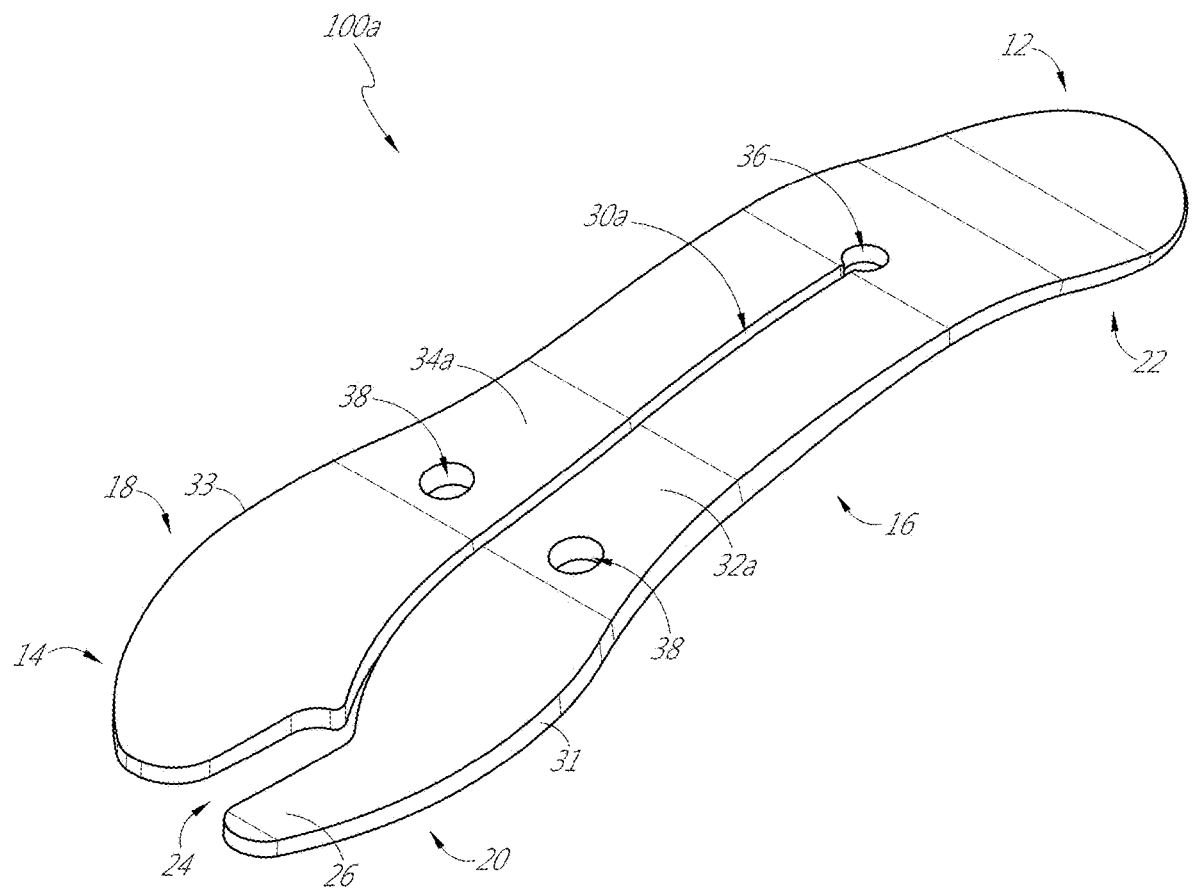
FIGS. 2A-4C illustrate example embodiments of foot elements.
Figure 2B:
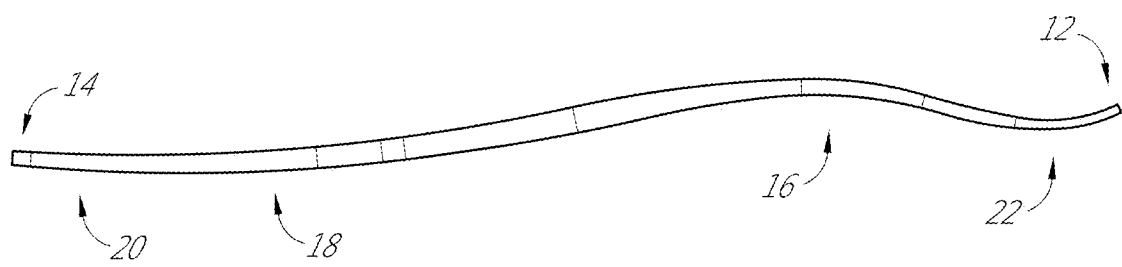
Figure 2C:
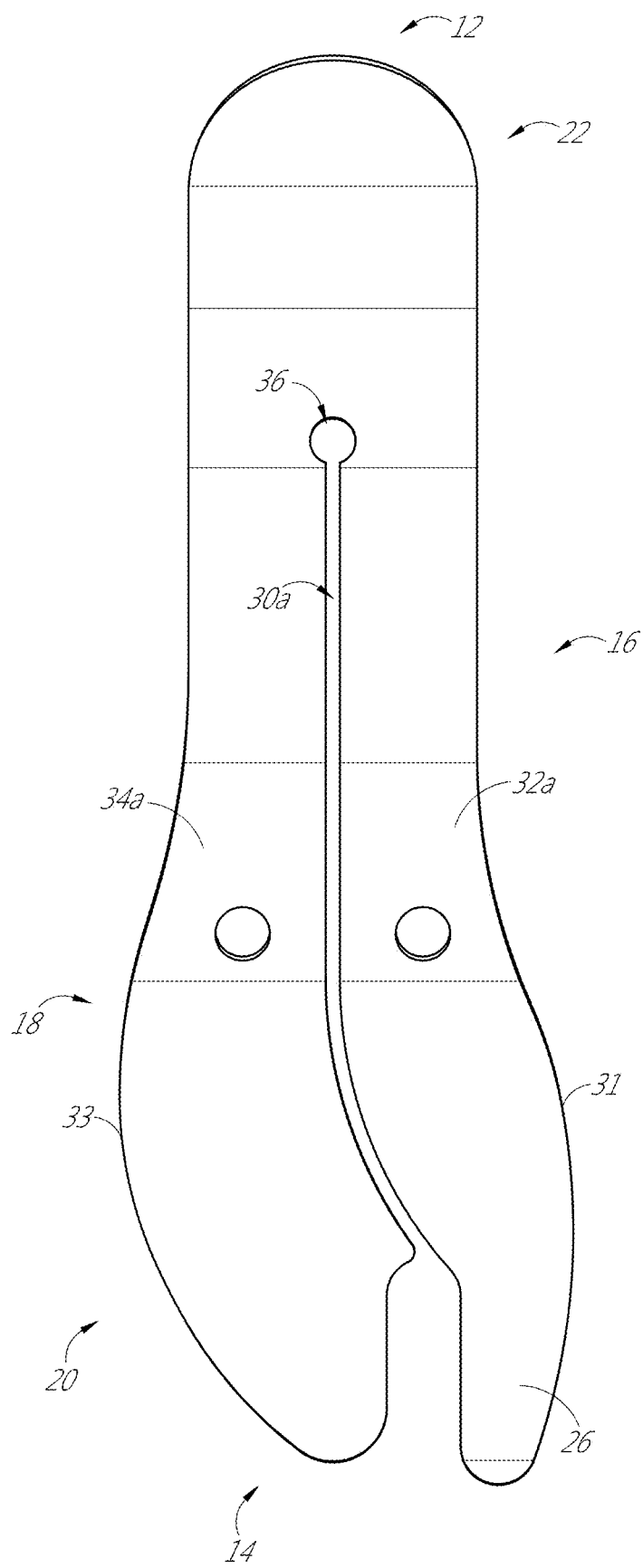
Figure 3A:
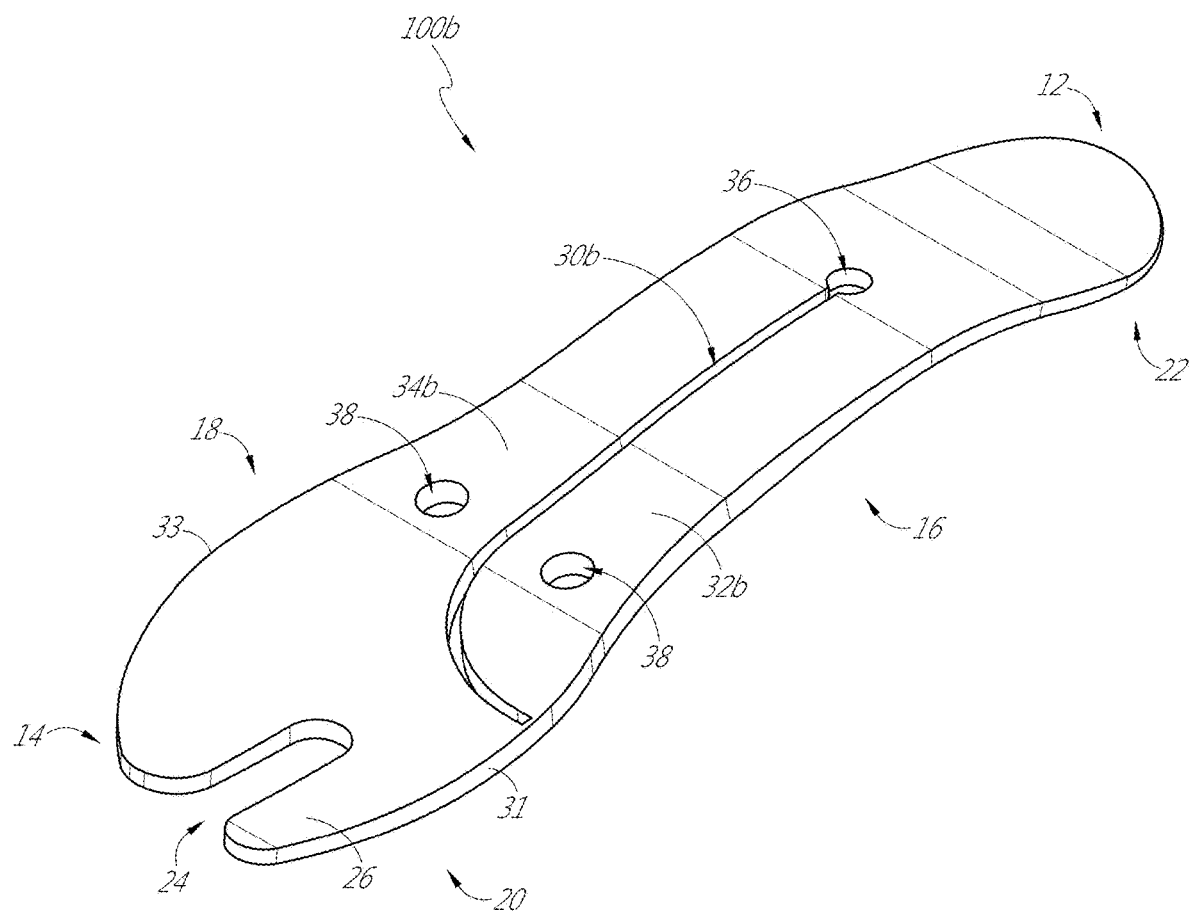
Figure 3B:
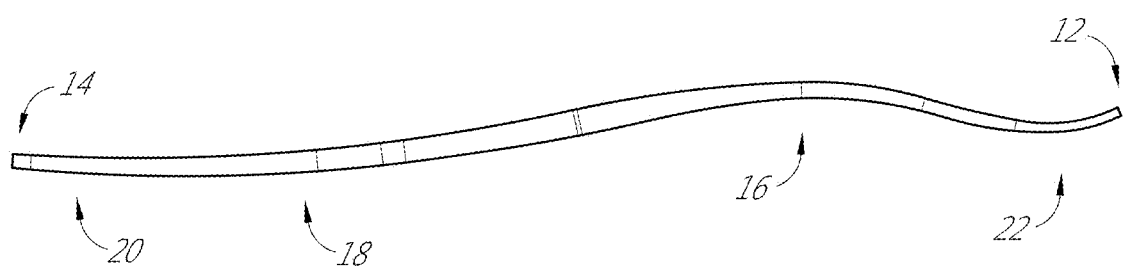
Figure 3C:
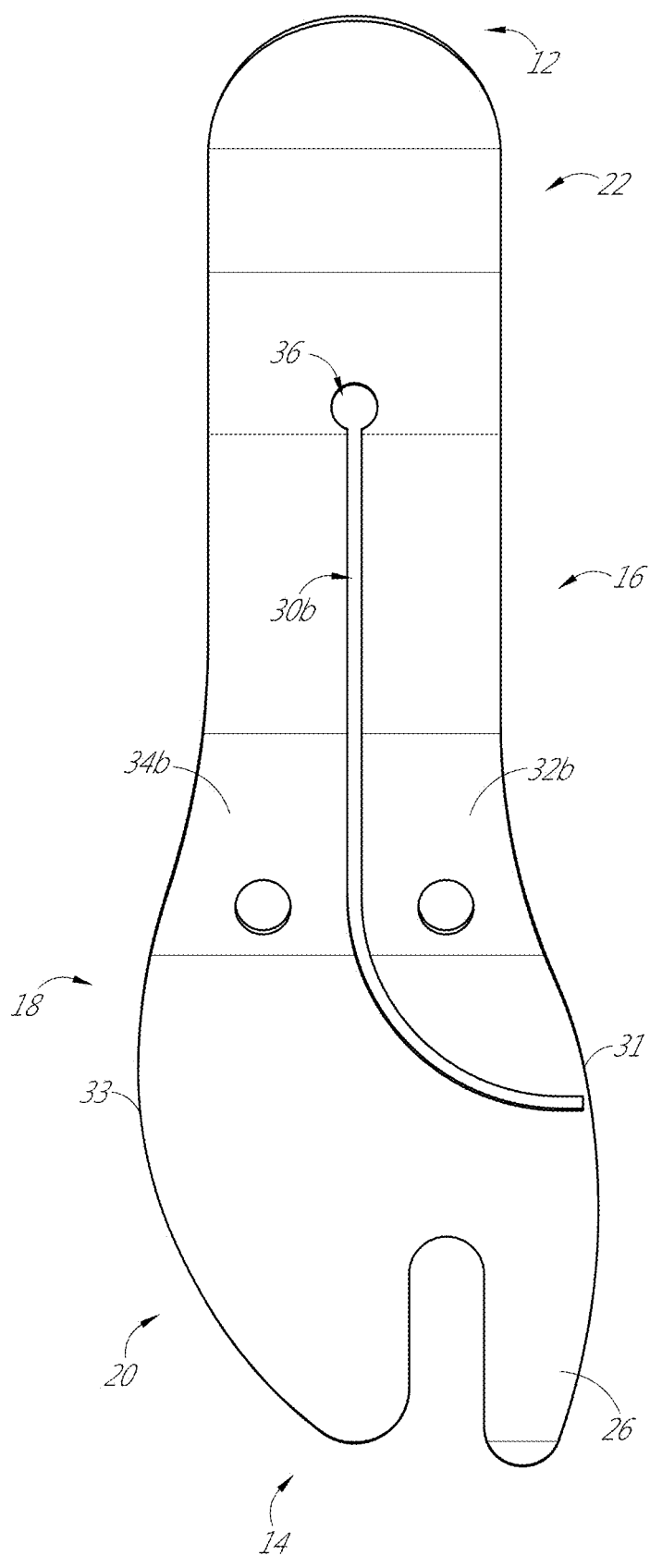
Figure 4A:
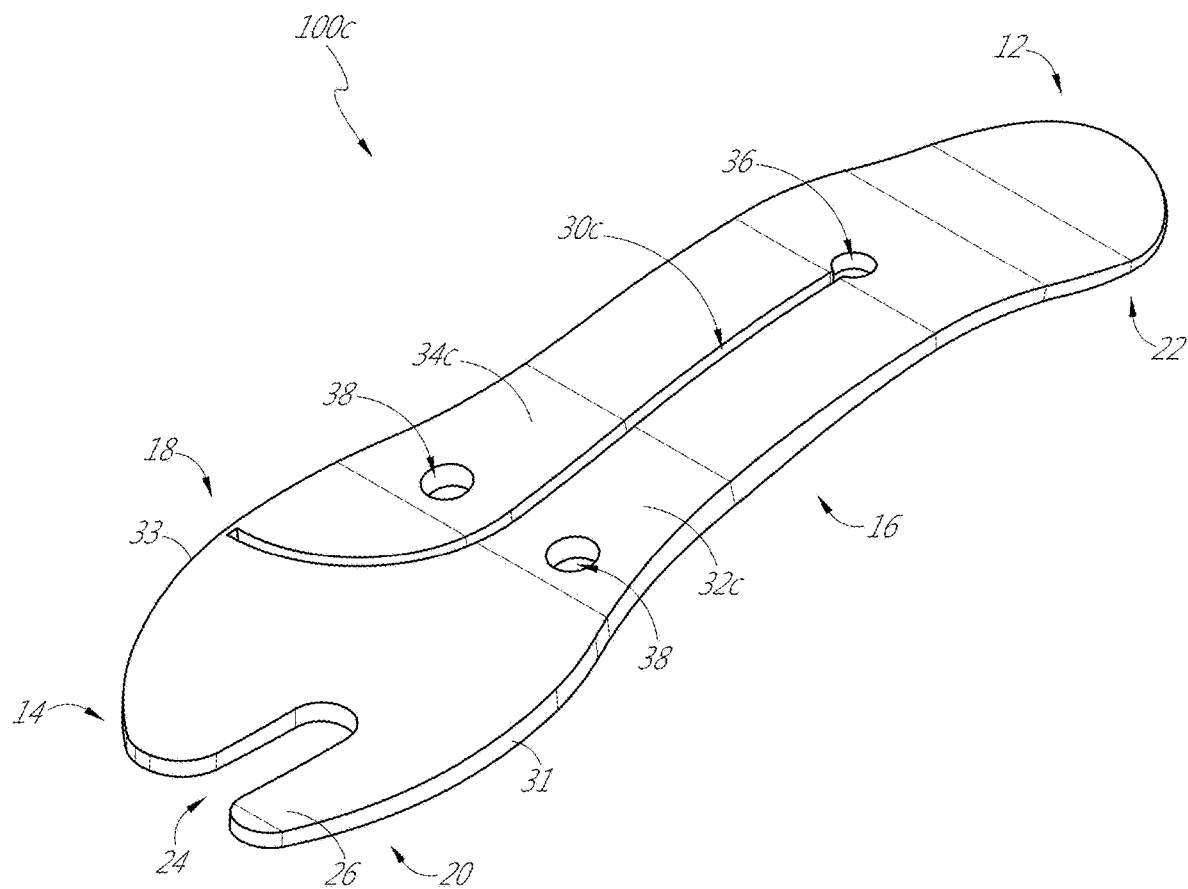
Figure 4B:
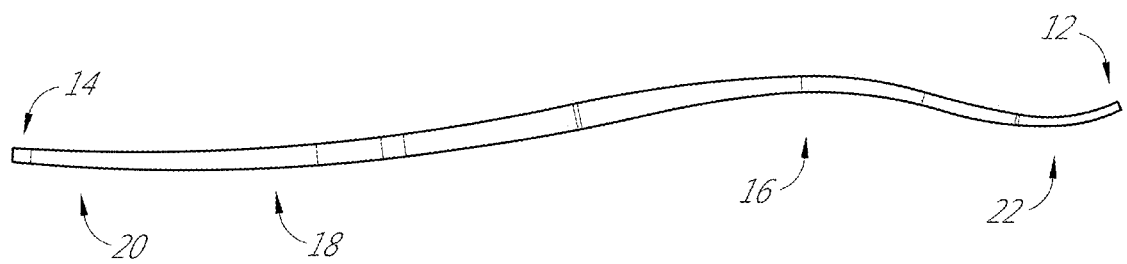
Figure 4C:
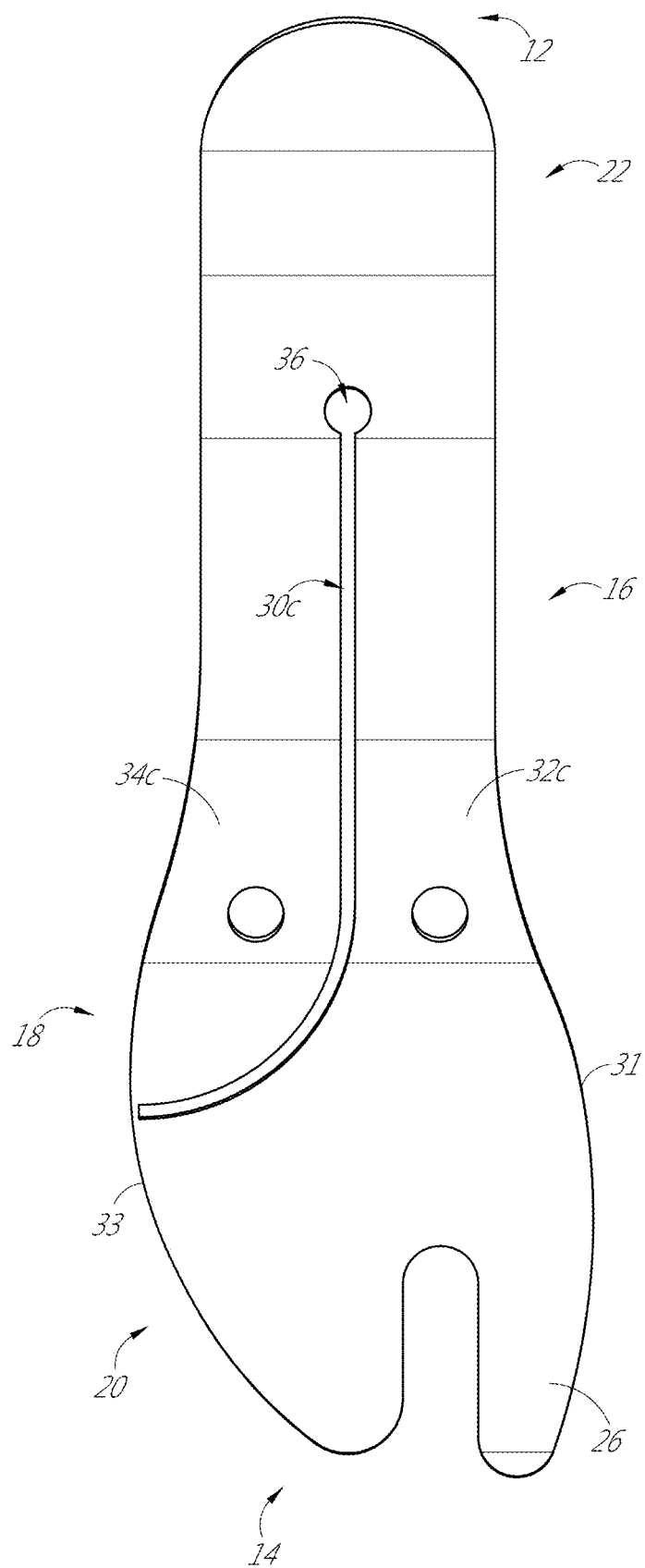

In the foot element 100a shown in FIGS. 2A-2C, the split 30a extends substantially straight from the opening 36 through the arch region 16, then curves medially in the forefoot region 18 or approximately at a border between the arch region 16 and the forefoot region 18. In the illustrated embodiment, the split 30a extends to or toward the cut out 24. In the foot element 100b shown in FIGS. 3A-3C, the split 30b similarly extends substantially straight from the opening 36 and curves medially in the forefoot region 18 or approximately at a border between the arch region 16 and the forefoot region 18. However, the split 30b of the foot element 100b of FIGS. 3A-3C curves more sharply than the split 30a of the foot element 100a of FIGS. 2A-2C and extends to or towards the medial edge 31 of the foot element 100b in the forefoot region 18. In the foot element 100c shown in FIGS. 4A-4C, the split 30c again extends substantially straight from the opening 36 and curves in the forefoot region 18 or approximately at a border between the arch region 16 and the forefoot region 18. However, the split 30c of the foot element 100c of FIGS. 4A-4C curves more sharply laterally and extends to or towards a lateral edge 33 of the foot element 100c in the forefoot region 18. The asymmetric split 30a, 30b, 30c can advantageously provide a rollover that more closely approximates or mimics that of a natural human foot. Although in the illustrated embodiments the split 30a, 30b, 30c extends substantially straight and parallel to a longitudinal axis of the foot element 100a, 100b, 100c from the opening 36 to the curved portion, in other embodiments, the split 30a, 30b, 30c can be nonparallel (e.g., angled, askew, curved, or otherwise not straight and/or not parallel to the longitudinal axis of the foot element 100a, 100b, 100c) along any portion between the opening 36 and curved portion.

In the embodiment of FIGS. 2A-2C, the split 30a separates the portion of the forefoot region 18 associated with the big toe 26 (e.g., the "ball" of the foot associated with the big toe) from the remainder of the forefoot region 18. This can advantageously allow the foot element 100a to more closely approximate or mimic a natural human foot. In some embodiments, the foot element 100a, 100b, 100c includes attachment holes 38 as discussed in greater detail herein. In some such embodiments, the curved portion of the split 30a, 30b, 30c begins distal to (or closer to the toe end 14 than) the attachment holes 38. In some embodiments, the curved portion of the split 30a, 30b, 30c begins proximal to (or closer to the heel end 12 than) the forefoot region 18 or at or proximal to a transition between the arch region 16 and the forefoot region 18.

In some embodiments, the portion of the foot element 100a, 100b, 100c that does not include the split 30a, 30b, 30c is between about 10% and about 30% of the total length of the foot element 100a, 100b, 100c (i.e., the length of the split 30a, 30b, 30c is between about 70% and about 90% of the length of the foot element 100a, 100b, 100c). In other words, the combined length of the portions of the foot element 100a, 100b, 100c from the opening 36 to the heel end 12 and from the end of the split 30a, 30b, 30c to the toe end 14 is no more than 30% and no less than 10% of the total length of the foot element 100a, 100b, 100c.

FIGS. 12A-12E illustrate an example embodiment of a foot element 400 that includes a drop-toe or vertically offset toe portion. In the illustrated embodiment, a forefoot piece 410 is coupled, either permanently or removably, to a bottom surface of at least a portion of the forefoot region 418 and/or toe portion 420 of the foot element 400. In the illustrated embodiment, the foot element 400 is similar to foot element 100a and includes a split 430 extending to a cut-out 424. However, in other embodiments, other variations of foot elements, include foot elements 100b, 100c shown and described herein, can include a forefoot piece and/or features shown and described herein with respect to the embodiment of FIGS. 12A-12E. As shown in the illustrated embodiment, the bottom surface of the forefoot region 418 and toe portion 420 can be flattened or straight (rather than curved) to accommodate a forefoot piece 410 having a flat or straight upper surface. In other embodiments, the bottom surface of the forefoot region 418 and toe portion can be curved or partially curved to accommodate a forefoot piece 410 having a curved or partially curved upper surface. As shown, the forefoot piece 410 is generally sized and shaped to correspond to the forefoot region 418 and/or toe portion 420 of the foot element, and a distal end of the forefoot piece 410 can include a cut-out 425 that corresponds in shape and size to the cut-out 424 of the foot element 400.

In the illustrated embodiment, a bottom surface of the forefoot piece 410 is curved or downward-facing convex. In some embodiments, the bottom surface of the forefoot piece 410 has a curvature that is discontinuous relative to and/or different from the curvature of the lower surface of the foot element 400 proximal to the forefoot piece 410. The bottom surface of the forefoot piece 410 may therefore be downwardly vertically offset from a remainder of the foot element 400 proximal to the forefoot piece 410. The forefoot piece 410 can advantageously allow for the foot element 400 to be supported during stance at portions of the heel and toe portion 420 rather than at the heel and fasteners that couple an upper foot member to the foot element 400. This allows for enhanced suspension and increased vertical displacement of the foot element 400 during stance because the fasteners are not in contact with the ground.

In some alternative embodiments, the forefoot piece 410 can be integrally formed with the foot element 400. In other words, the bottom surface of the forefoot region 418 and/or toe portion 420 of the foot element 400 itself can form or define a curvature that is different than and/or discontinuous relative to the curvature of the lower surface of the foot element 400 proximal to the forefoot region 418 and/or toe portion 420. In some embodiments, an upper surface of the forefoot region 418 and/or toe portion 420 can also define a curvature that is different than and/or discontinuous relative to the curvature of the upper surface of the foot element 400 proximal to the forefoot region 418 and/or toe portion 420. Additional details regarding drop-toe or vertically offset toe portions can be found in U.S. Publication No. 2013/0144403, the entirety of which is hereby incorporated herein by reference.

Figure 6:
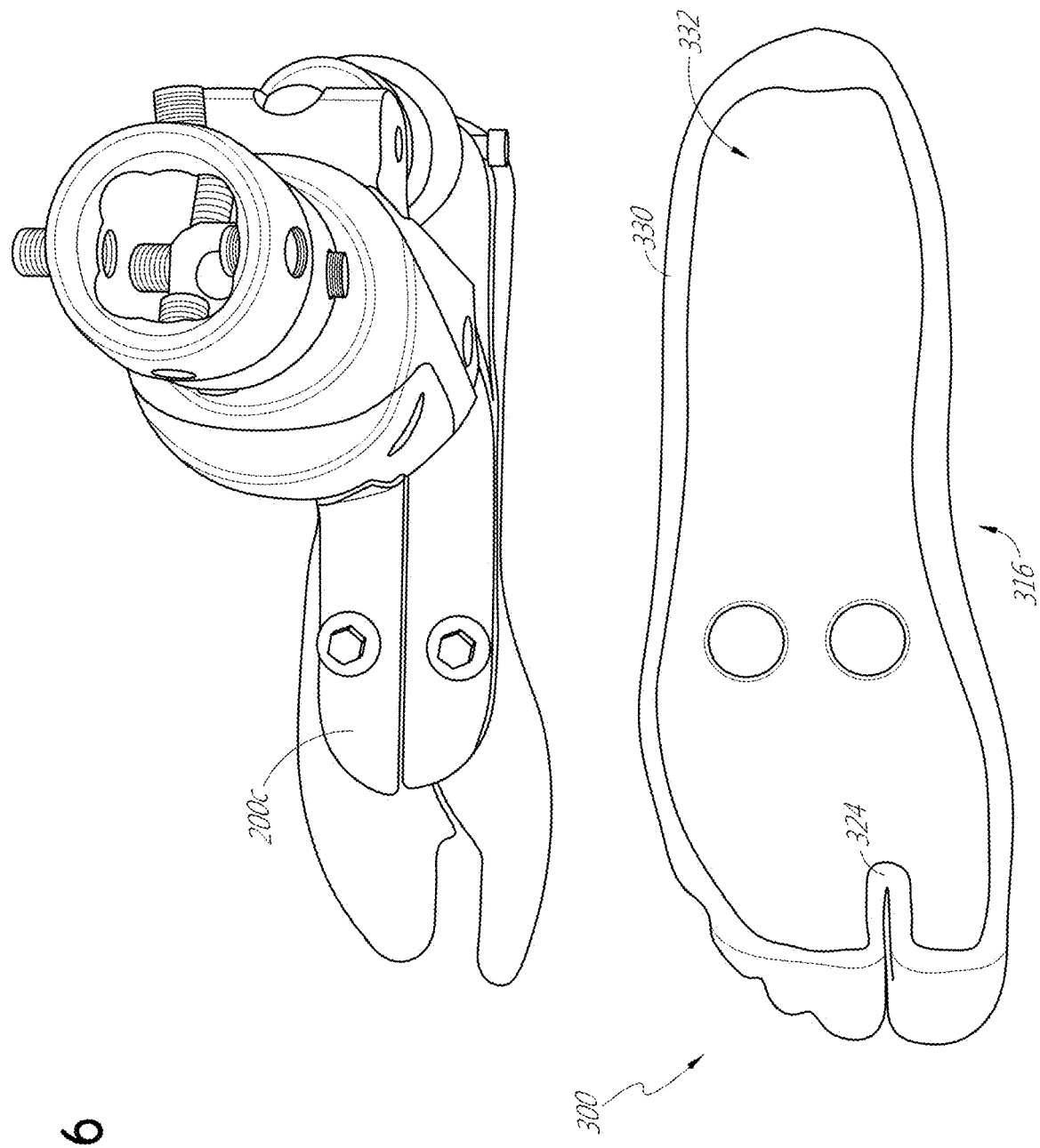
FIG. 6 illustrates an example embodiment of a prosthetic foot incorporating the foot element of FIGS. 2A-2C and a top view of an example embodiment of a foot cover configured to receive a prosthetic foot.
Figure 7:
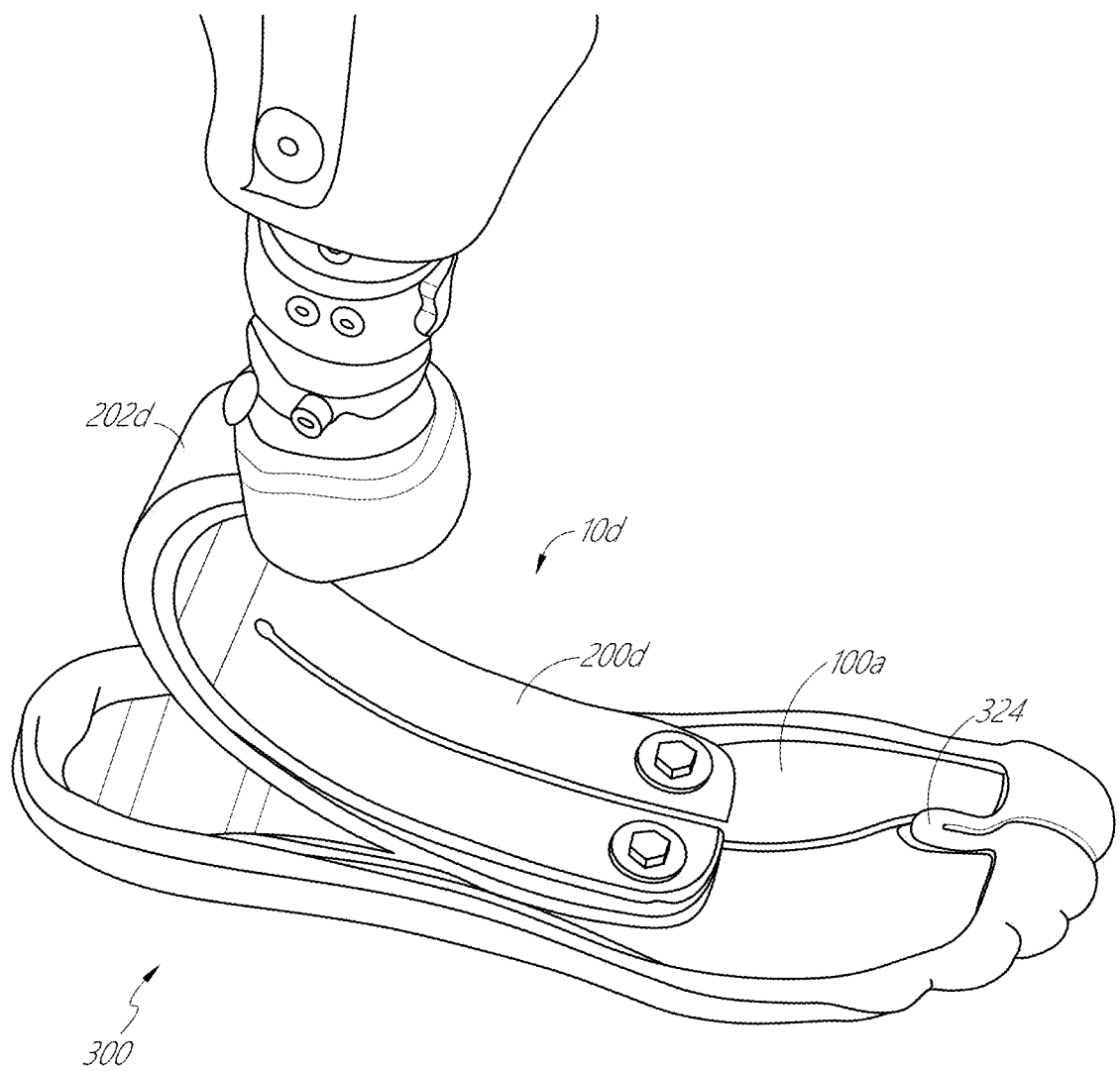
FIG. 7 illustrates an example embodiment of a prosthetic foot incorporating the foot element of FIGS. 2A-2C received in the foot cover of FIG. 6.

Foot elements according to the present disclosure, for example, foot elements 100a, 100b, 100c, can be incorporated into a variety of prosthetic feet, for example as shown in FIGS. 1 and 6-7. In some embodiments, foot elements 100a, 100b, 100c include attachment holes 38. An upper foot element, such as upper foot elements 200a-200f of the prosthetic feet 10a-10f shown in FIG. 1, can be coupled to the foot element 100a, 100b, 100c with fasteners, e.g., screws, bolts, or the like 40, inserted through the attachment holes 38. The upper foot elements 200a-200f can also include attachment holes to receive the screws, bolts, or the like 40. Alternatively, an upper foot element can be coupled to a foot element 100a, 100b, 100c with an adhesive or other suitable mechanism. Upper foot elements 200a-200f can be made or constructed with the same or similar materials and the same or similar processes as described herein with respect to foot element 100a, 100b, 100c.

Figure 1D:
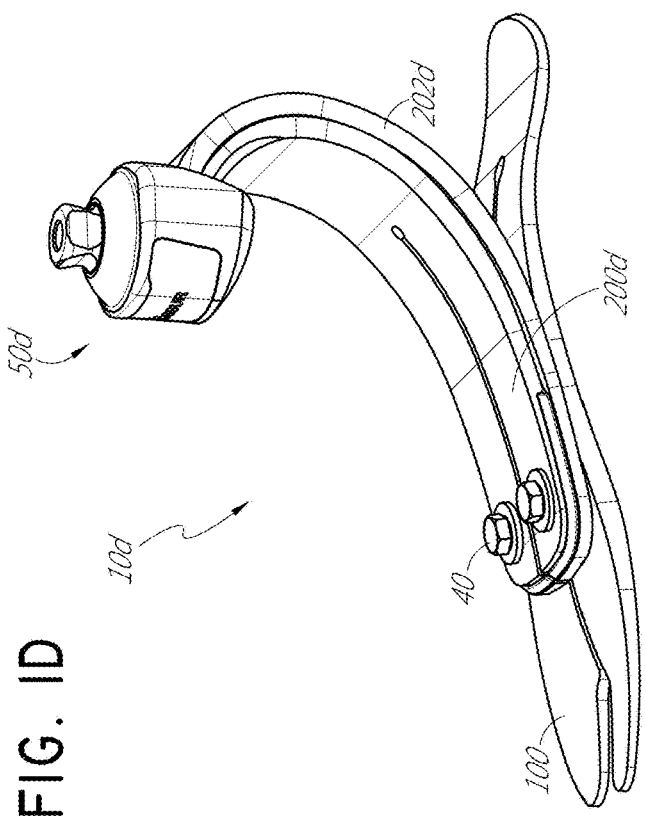

As shown, upper foot element 200b has a generally vertical proximal portion and extends downwards and forwards to a generally horizontal distal portion. The upper foot element 200b is coupled to the foot element 100 via bolts, screws, or the like 40 proximate a distal or anterior end of the upper foot element 200b. The upper foot element 200b therefore extends forward approximately to a transition area between the arch region 16 and the forefoot region 18. Upper foot element 200a is designed so that prosthetic foot 10a has a lower profile than prosthetic foot 10b. Upper foot element 200f is similar to upper foot element 200a. However, in the illustrated embodiment, upper foot element 200f has a tapered shape such that a distal end of the upper foot element 200f is thicker than a proximal end of the upper foot element 200f. The prosthetic foot 10f of FIG. 1F can also include an upper flex plate 204f. Additional details regarding prosthetic feet incorporating features similar to prosthetic foot 10f can be found in U.S. Provisional Application No. 62/153,406, filed Apr. 27, 2015, the entirety of which is hereby incorporated by reference herein. Upper foot element 200c has a C-shape, or has a relatively short concave-forward portion at or near the proximal end, though it can have other suitable shapes such as an L-shape or J-shape. In the illustrated embodiment, upper foot element 200c extends farther forward or anteriorly into the forefoot region 18 of the foot element 100 than upper foot elements 200a, 200b, as also shown in FIG. 6. In the illustrated embodiment, upper foot element 200c also has a curved distal end, whereas upper foot elements 200a, 200b have straight distal ends. Any of the upper and/or intermediate foot elements described herein can have straight or curved distal ends. Prosthetic foot 10c also includes an intermediate element 202c positioned between the upper foot element 200c and the foot element 100. Prosthetic foot 10e similarly includes an upper foot element 200e having a concave-forward portion at or near the proximal end, although other shapes for upper foot element 200e are also possible such as an L-shape or J-shape, and an intermediate element 202e positioned between the upper foot element 200e and the foot element 100. As shown in FIGS. 1C and 1E, the proximal ends of the upper foot members 200c, 200e can be coupled to a front portion 212c, 212e of an ankle module 210c, 210e, and the proximal ends of the intermediate elements 202c, 202e can be coupled to a rear portion 214c, 214e of the ankle module 210c, 210e, which may be, for example, a support member, actuator, or rod connector. FIGS. 1D and 7 illustrate an example embodiment of a prosthetic foot 10d having dual C-shaped upper foot elements 200d, 202d. The upper and/or intermediate foot elements shown in FIGS. 1 and 6-7 can be used with any foot element according to the present disclosure, such as foot elements 100a, 100b, 100c. Additionally, foot elements according to the present disclosure, such as foot elements 100a, 100b, 100c, can be used with other configurations of upper and/or intermediate foot elements and can be incorporated into a variety of prosthetic feet.

Figure 1F:
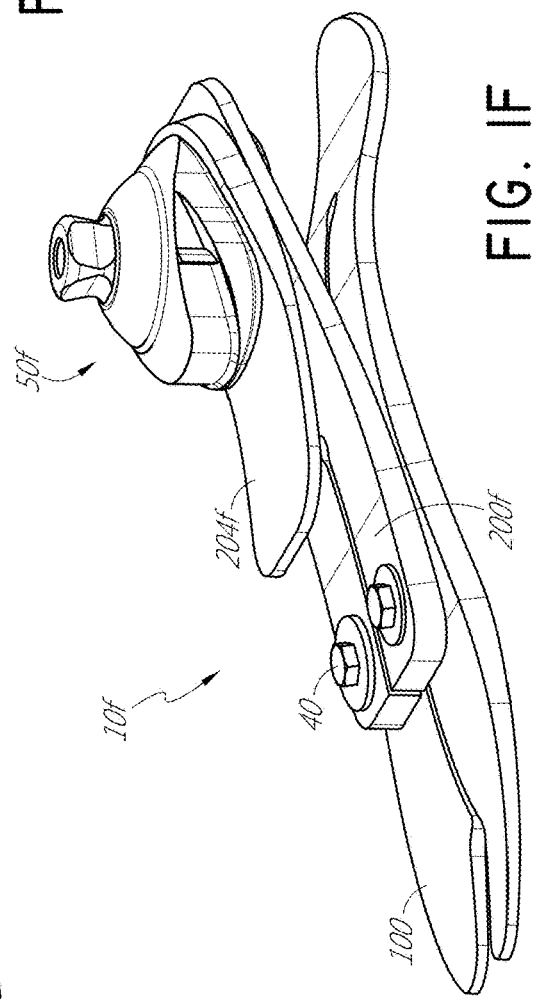

As shown in FIGS. 1A-1F, prosthetic feet incorporating foot elements 100a, 100b, 100c, such as prosthetic feet 10a-10f, can also include an adapter configured to couple the prosthetic foot to a user, for example, to the user's residual limb, a pylon, or another prosthetic component. For example, FIG. 1A illustrates an example embodiment of an adapter 50a coupled to a proximal end of upper foot member 200a of prosthetic foot 10a, and FIG. 1B illustrates another example embodiment of an adapter 50b coupled to a proximal end of upper foot member 200b of prosthetic foot 10b. FIGS. 1C and 1E illustrate example embodiments of adapters 50c, 50e, respectively, coupled to proximal ends of ankle modules 210c, 210e, respectively. In the example embodiment of FIG. 1D, another example embodiment of an adapter 50d is coupled to the proximal ends of the dual upper foot elements 200d, 202d. FIG. 1F illustrates an example embodiment of an adapter 50f coupled to the proximal end of the upper flex plate 204f. Other configurations and arrangements of adapters are also possible.

Figure 8:
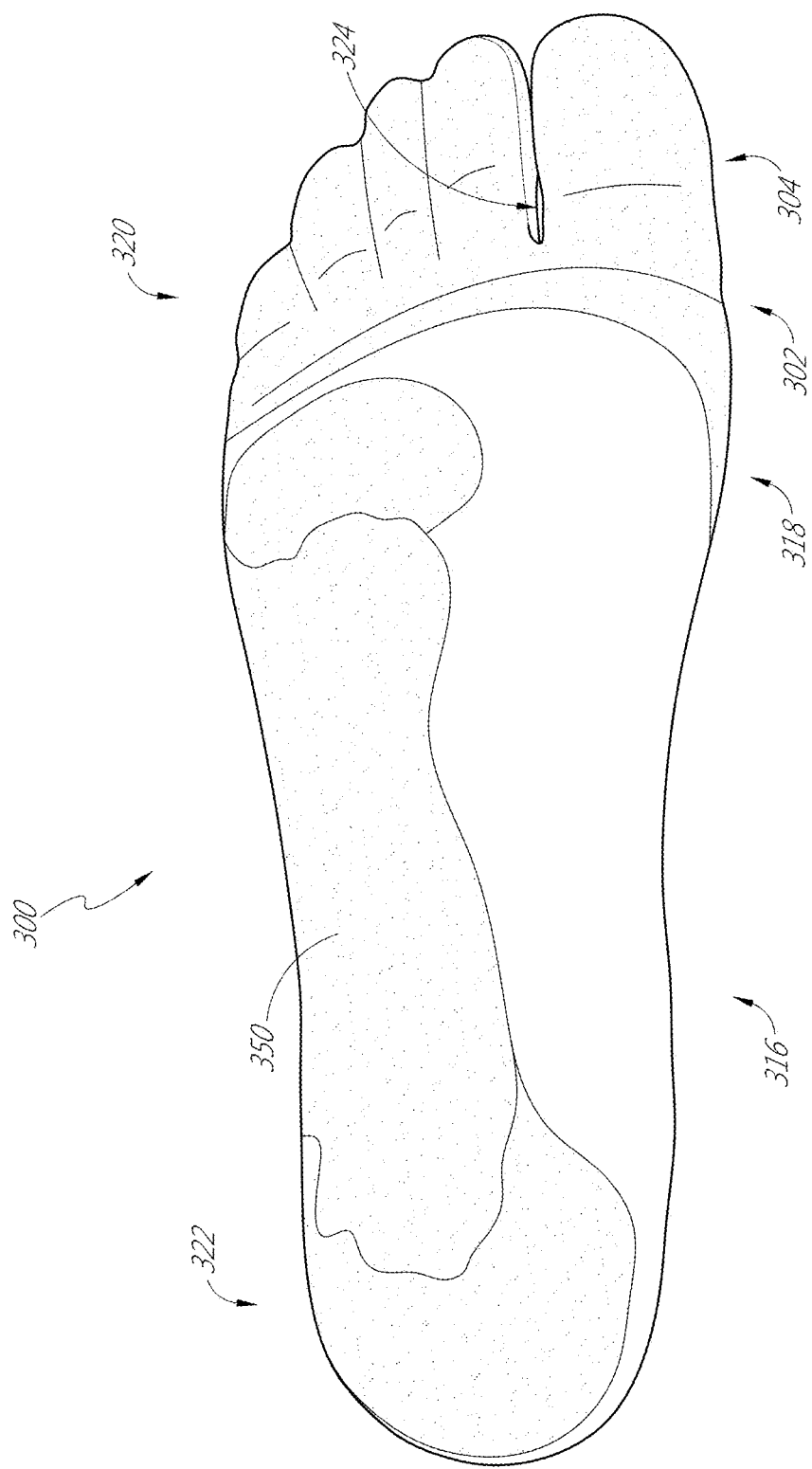
FIG. 8 illustrates a bottom view of the foot cover of FIGS. 6-7.
Figure 13B:
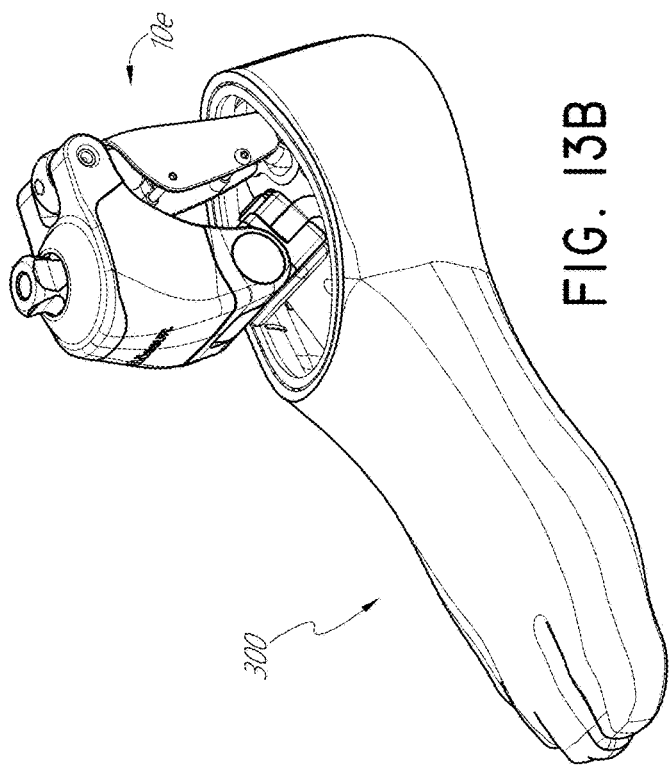
FIGS. 13A-13C illustrate example embodiments of prosthetic feet disposed in an example embodiment of a foot cover.
Figure 13A:
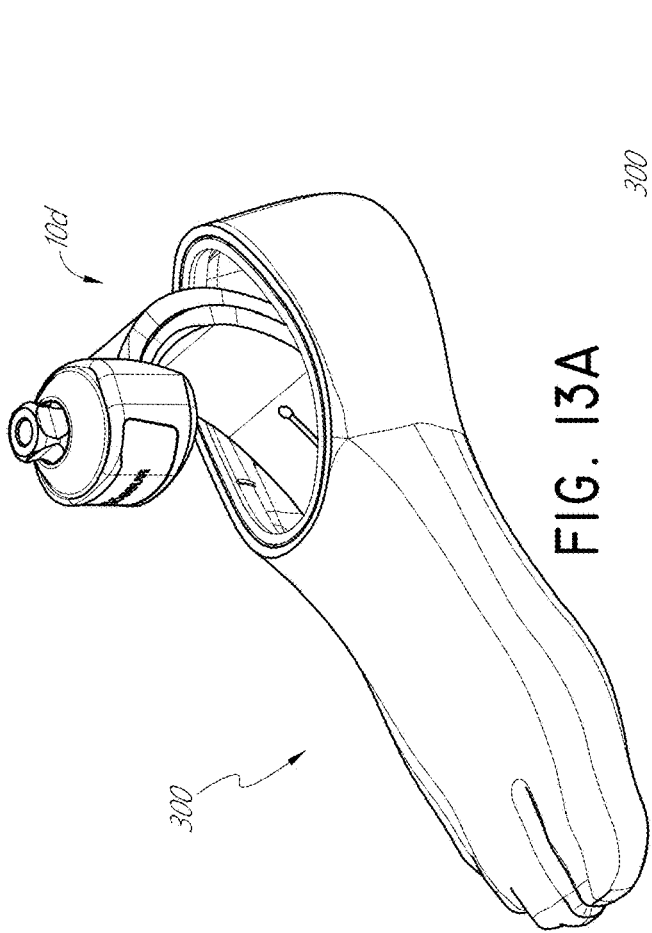
Figure 13C:
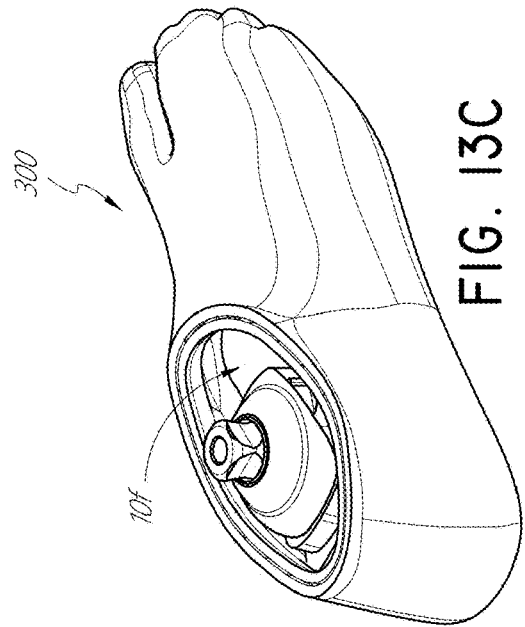

FIGS. 6-8 illustrate an example embodiment of a cosmesis or foot cover 300 designed to receive a prosthetic foot, such as a prosthetic foot as described herein. The foot cover 300 has the shape of a natural human foot, which can advantageously improve the aesthetic appeal of a prosthetic foot. The foot cover 300 is also designed to enhance the performance of the prosthetic foot. In some embodiments, the foot cover 300 is made of polyurethane or a similar material, although other materials are also possible. The foot cover 300 has an outer body 330 having an opening at a top end and defining and surrounding an inner cavity 332 that removably receives a prosthetic foot. The outer body 330 includes a sole portion and sidewalls extending upward from the sole portion to form sides and a top of the outer body 330. In some embodiments, the sole portion and sidewalls are integrally formed such that the outer body 330 is monolithic. An outer surface of the body generally has the shape and contours of a natural human foot to give the cosmesis the appearance of a natural human foot. In the illustrated embodiment, the foot cover 300 is shallow; in other words, the sidewalls are short and do not extend upward far beyond a level of a foot when received in the foot cover 300 (e.g., the sidewalls of the foot cover extend to a level below that corresponding to the ankle in a natural human foot). In other embodiments, the sidewalls extend to a level corresponding to that of the ankle of a natural human foot, for example, as shown in FIGS. 10 and 13A-13C. FIGS. 13A-13C illustrate prosthetic feet 10d, 10e, and 10f, respectively, disposed in the foot cover 300. In yet other embodiments, the sidewalls can extend higher than the level of the ankle. Additional details on foot covers can be found in U.S. Pat. No. 8,128,709, entitled "Functional Foot Cover," and U.S. Pat. No. 8,685,109, entitled "Smooth Rollover Insole for Prosthetic Foot," the entireties of which are hereby incorporated by reference and should be considered a part of this specification.

In some embodiments, the foot cover 300 includes areas having relatively greater flexibility in a forefoot 318 and/or toe region 320, for example as shown in FIG. 8. In some embodiments, the areas of greater flexibility are formed by areas that are thinner than the remainder of the foot cover 300. Additionally or alternatively, the regions of greater flexibility can be made of a different material than the remainder of the foot cover 300. In the illustrated embodiment, the foot cover 300 includes a region 302 of increased flexibility at a transition area between the forefoot or ball of the foot region 318 and the toe region 320, for example, at an area corresponding to the metatarsal joint of a natural human foot. In the illustrated embodiment, the foot cover 300 also includes regions 304 of increased flexibility in the toe region 320, for example, at areas corresponding to joints between bones of the toes in a natural human foot. These areas of increased flexibility can advantageously allow the toe portion 320 of the foot cover 300 to articulate relative to the forefoot region 318 to more closely resemble a natural human foot.

In some embodiments, an arch region 316 of the foot cover 300 is designed to more closely resemble that of a natural human foot. In some embodiments, the foot cover 300 includes padded areas or areas of increased build at or around a heel region 322, an outer portion of the arch region 316, and/or the forefoot or ball of the foot region 318, for example as shown in FIG. 8. In the illustrated embodiment, the foot cover 300 includes a padded area 350 extending from the heel region 322, across an outer or lateral portion of the arch region 316, to an outer or lateral portion of the forefoot or ball of the foot region 318. In other embodiments, the foot cover 300 can include padded areas at other locations of the foot cover 300.

In some embodiments, the foot cover 300 is designed to be used with a prosthetic foot including a foot element such as foot elements 100a, 100b, 100c as described herein. For example, the foot cover 300 can include a mating structure or slot 324 that engages the cutout 24 of the foot element 100a, 100b, 100c as shown in FIG. 7. The slot 324 can allow the foot cover 300 to more closely resemble a human foot. The slot 324 can also receive a strap of a sandal. The foot cover 300 can also or alternatively define several toes disposed adjacent each other without intervening slots therebetween. In some embodiments, the foot cover 300 and foot element 100a, 100b, 100c are designed to correspond in size and shape to one another such that the foot cover 300 and foot element 100a, 100b, 100c have an improved fit (e.g., the perimeter of the foot plate substantially coincides with the perimeter of the inner sole in the foot cover on which the foot plate is positioned). With previously available prosthetic feet and foot covers, the foot is usually not the same shape and/or size as the foot cover, so there is often empty or extra space within the foot cover (e.g., the perimeter of the foot plate does not coincide with the perimeter of the inner sole in the foot cover on which the foot plate is positioned), which can cause wear and tear in the foot cover and/or suboptimal performance. With the foot elements 100a, 100b, 100c and foot cover 300 of the present disclosure, all or substantially all of the sole portion of the foot cover 300 corresponds to a portion of the foot element 100a, 100b, 100c such that any space between the foot plate and the foot cover is reduced or minimized. This advantageously allows the foot element 100a, 100b, 100c and foot cover 300 to work together and improves or optimizes the functionality of the foot cover 300.

Figure 9:
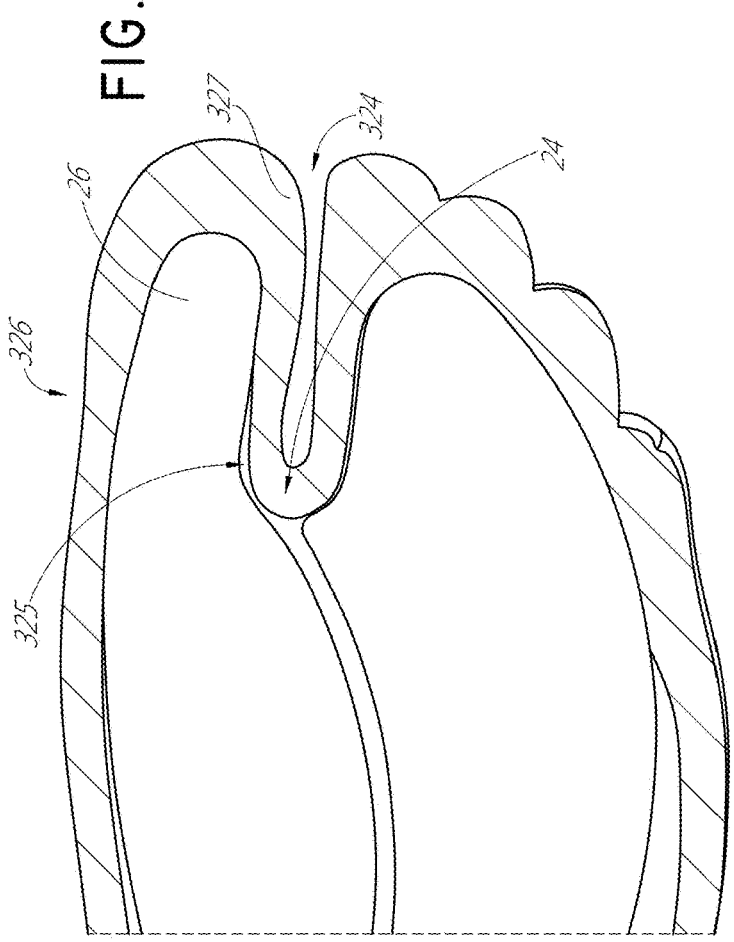
FIG. 9 illustrates a partial cross-sectional view of a foot element received in a foot cover.

In some embodiments, for example as shown in FIG. 9, an inner surface 325 of a big toe portion 326 of the foot cover can have a slightly different shape than the big toe 26 of the foot element. The portion 327 of the wall of the big toe portion 326 adjacent the slot 324 can also have an increased thickness. As shown in FIG. 9, the big toe 26 can angle slightly laterally (or toward the cut-out 24). When the foot element is placed in the foot cover, due to the angled big toe 26, shape of the inner surface 325, and/or increased thickness of the portion 327 of the wall of the big toe portion 326, the big toe portion 326 of the foot cover is pushed toward the remaining "toes" of the foot cover, which at least partially closes the slot 324. This can advantageously help hold a sandal strap in place and help inhibit the sandal from falling off during gait, which is a problem users often face with existing foot covers.

Figure 10:
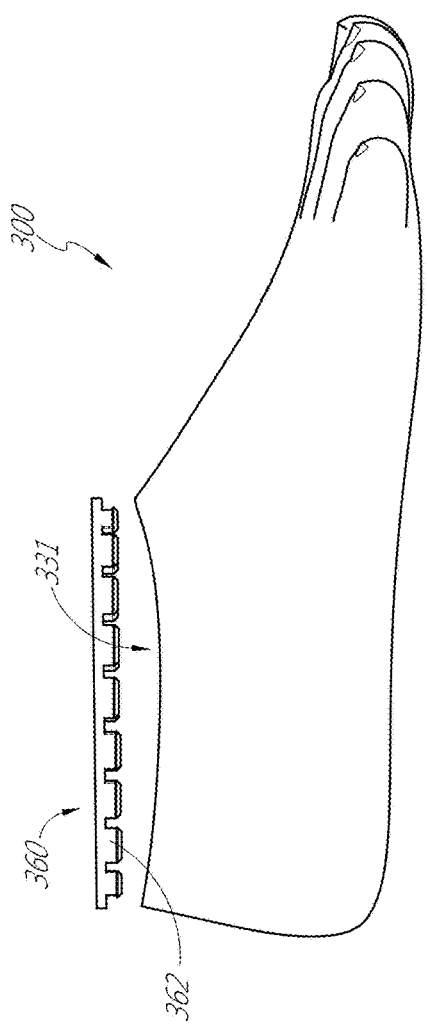
FIG. 10 illustrates an example embodiment of a foot cover and an attachment member.
Figure 12A:
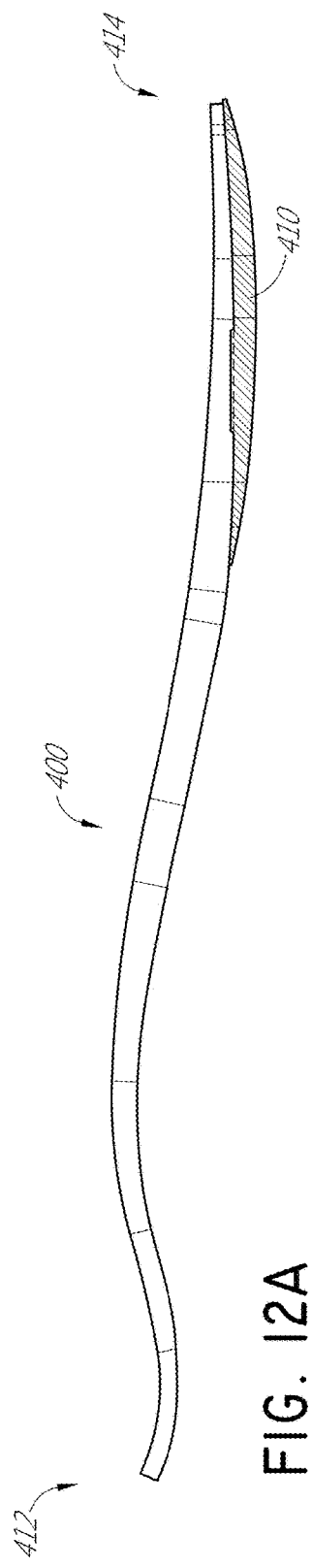
FIGS. 12A-12E illustrate an example embodiment of a foot element including a drop-toe portion.
Figure 12B:
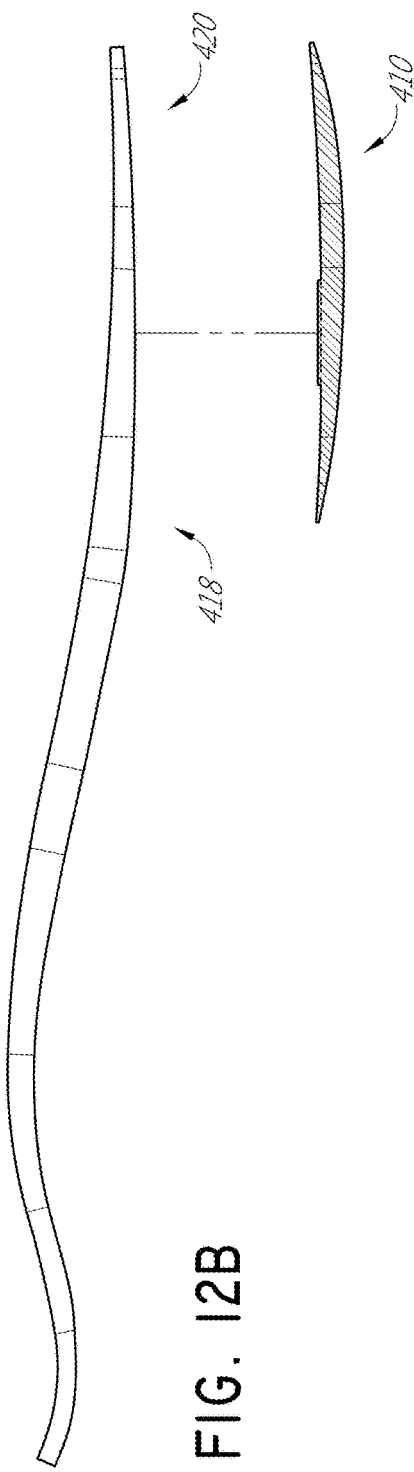
Figure 12D:
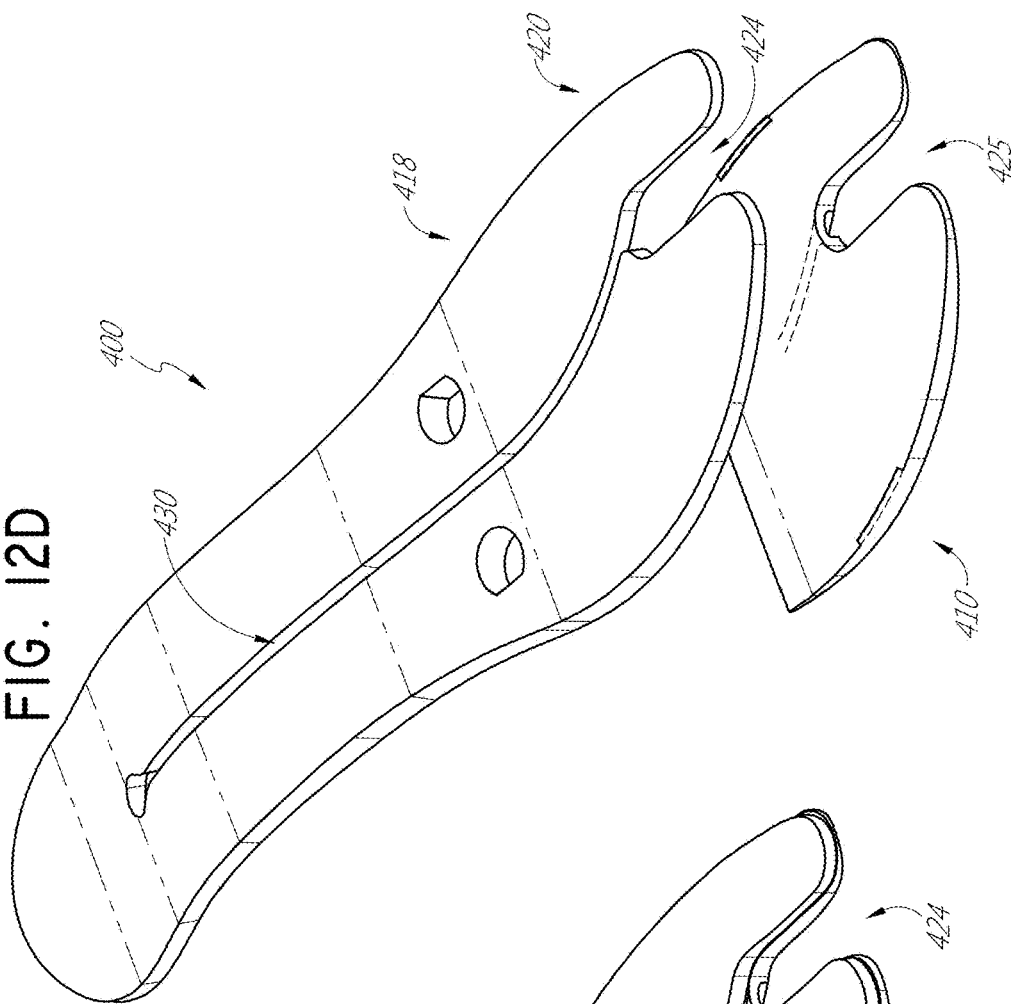
Figure 12C:
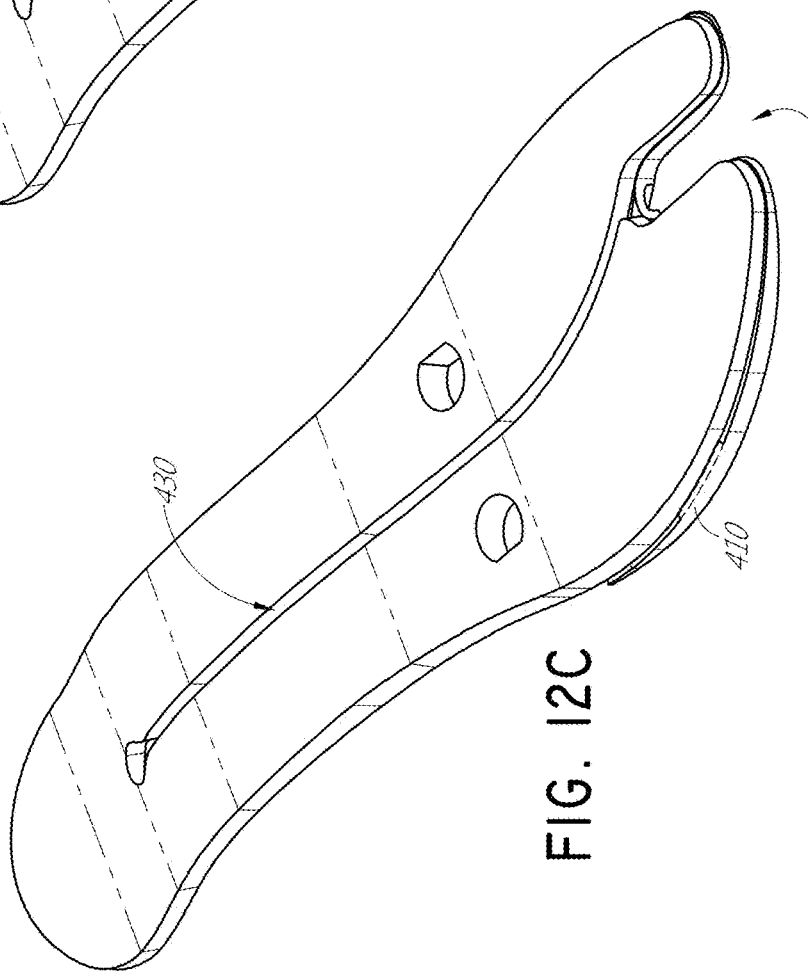
Figure 12E:
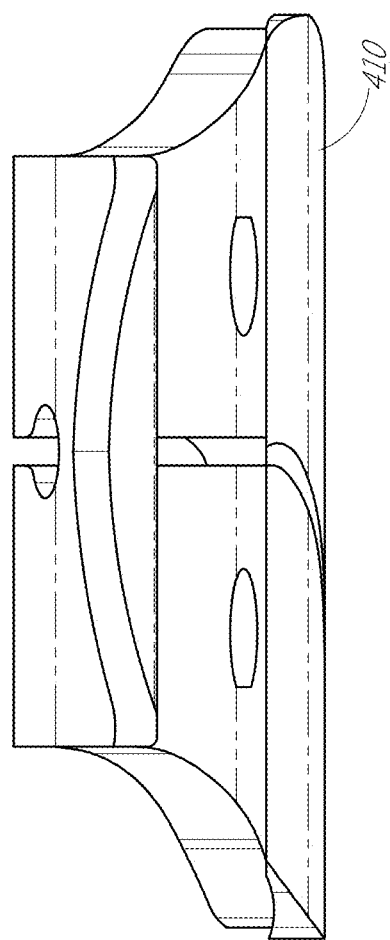

As shown in FIG. 10, in some embodiments, the top opening 331 of the foot cover 300 is curved or concave rather than straight. The concave profile can advantageously provide for a more secure attachment of a flat or straight attachment plate 360 to the main body of the foot cover. The attachment plate 360 includes downwardly extending teeth or pins 362 configured to fit into cavities in the rim of the top opening 331. As the attachment plate 360 is coupled to the rim, the attachment plate 360 is bent or curved to fit the curved opening, and the teeth or pins 362 spread outwardly and upwardly. This can increase the holding strength of the pins 362 in the cavities and increase the pull force needed to detach the attachment plate 360 from the foot cover 300, particularly, for example, at the front and rear portions of the opening 331. The curved opening 331 can also improve the aesthetic appearance of the foot cover 300 as the curve resembles the shape of the opening of a shoe.

In some embodiments, the forefoot region 318 of the foot cover 300 is wider than a remainder of the foot cover 300, for example, wider than the arch region 316 and/or heel region 322, and wider than previously available prosthetic feet and/or foot covers. In some cases, conventional or previously available prosthetic feet and foot covers have poor compliance with shoes designed for natural human feet. The forefoot regions of such feet and/or foot covers are often narrower than natural human feet, so there is often a space between the foot cover and shoe. The space or gap allows for movement between the foot or foot cover and shoe, which can result in wear on the foot and/or foot cover. The wider forefoot region 18 of the foot element 100a, 100b, 100c and the corresponding wider forefoot region 318 of the foot cover 300 can advantageously help reduce such wear. The wider forefoot region can also improve the aesthetic appearance of the foot and/or foot cover as it can resemble the size and/or shape of a natural human foot more closely.

In some embodiments, for example as shown in FIGS. 11A-11B, an inner surface of the sole portion of the foot cover 300 includes dimples or perforations 370. The dimples 370 advantageously allow for the creation of more even material thickness, particularly in relatively thick portions of the sole portion. The dimples 370 allow the material to cool more quickly and evenly without distortion during production of the foot cover 300. The dimples 370 also reduce the mass of the foot cover 370.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A prosthetic foot comprising:
   an elongate foot element extending from a heel end to a toe end, wherein a width of a forefoot portion of the foot element is greater than a width of an arch region and a heel region, the foot element comprising a generally U-shaped cut-out portion at the toe end that is positioned toward a medial side of a longitudinal axis of the foot element, the cut-out portion dividing the toe end into a medial toe and a lateral toe portion, the medial toe being longer and extending further distally than the lateral toe portion; and
   a cosmesis cover comprising a body having an outer surface and surrounding an inner cavity, the outer surface having the shape and contours of a natural human foot, the inner cavity configured to removably receive the foot element therein, the cosmesis having a heel region, arch region, forefoot region, and toe region, wherein the forefoot region is relatively wider than the heel region and the arch region, and the cosmesis having an inner sole portion and a sidewall extending upward from the inner sole portion, wherein the cosmesis cover further comprises a padded area on an outer bottom surface of the body extending from the heel region and across a lateral part of the arch region and the forefoot region of the cosmesis cover, the padded area comprising an increased build relative to an adjacent portion of the outer bottom surface on a medial part of the arch region and the forefoot region of the cosmesis cover,
   wherein a size and shape of the inner sole portion and portion of the sidewall adjacent the inner sole portion substantially corresponds to a size and shape of the foot element.

2. The prosthetic foot of claim 1, the toe region of the cosmesis further comprising a mating structure configured to engage the cut-out portion of the foot element.

3. The prosthetic foot of claim 1, the foot element further comprising a lengthwise split, wherein a first portion of the split runs substantially straight in an anterior/posterior direction and a second portion curves in a medial direction and extends to a base of the cut-out portion.

4. The prosthetic foot of claim 3, wherein a juncture of the second portion of the split and the base of the cut-out portion comprises a blunted edge.

5. The prosthetic foot of claim 1, wherein the sidewall extends upward to approximately the level of an ankle of a natural human foot.

6. The prosthetic foot of claim 1, further comprising an upper foot element coupled to the foot element via fasteners inserted through one or more attachment holes in the foot element.

7. The prosthetic foot of claim 6, comprising an intermediate foot element located between the upper foot element and the elongate foot element.

8. The prosthetic foot of claim 7, comprising an ankle module coupled to the upper foot element and the intermediate foot element.

9. The prosthetic foot of claim 8, wherein a proximal end of the upper foot element is coupled to a front portion of the ankle module.

10. The prosthetic foot of claim 8, wherein a proximal end of the intermediate foot element is coupled to a rear portion of the ankle module.

11. The prosthetic foot of claim 8, wherein the ankle module is operably and indirectly coupled to the elongate foot element via the fasteners inserted through the one or more attachment holes.

12. The prosthetic foot of claim 1, wherein a width of the forefoot portion relative to a length of the foot element is about 30%.

13. The prosthetic foot of claim 1, wherein a width of the forefoot region relative to a length of the cosmesis cover is about 30%.

14. The prosthetic foot of claim 1, wherein the body comprises a region of increased flexibility at a transition between the forefoot region and the toe region.

15. The prosthetic foot of claim 14, wherein the region of increased flexibility is thinner than a remainder of the body.

16. The prosthetic foot of claim 1, comprising a forefoot piece at the toe end, a bottom surface of the forefoot piece forming at least a portion of a bottom surface of the elongate foot element, the forefoot piece having a medial toe portion and a lateral toe portion that align respectively with the medial toe and the lateral toe portion of the foot element.

17. The prosthetic foot of claim 1, wherein a surface of the inner sole portion of the cosmesis cover comprises a plurality of dimples or perforations across a width of the surface of the inner sole portion, wherein the plurality of dimples or perforations are spaced apart from each other across the width of the inner sole portion.

18. The prosthetic foot of claim 17, wherein the plurality of dimples or perforations are circular or substantially cylindrical.

\* \* \* \* \*